United States Patent [19]

Kriesel

[11] Patent Number: 5,205,820
[45] Date of Patent: Apr. 27, 1993

[54] FLUID DELIVERY APPARATUS

[75] Inventor: Marshall S. Kriesel, Saint Paul, Minn.

[73] Assignee: Science, Incorporated, Bloomington, Minn.

[21] Appl. No.: 870,269

[22] Filed: Apr. 17, 1992

Related U.S. Application Data

[63] Continuation of Ser. No. 642,208, Jan. 16, 1991, Pat. No. 5,169,389, which is a continuation-in-part of Ser. No. 367,304, Jun. 16, 1989, Pat. No. 5,019,047.

[51] Int. Cl.$^5$ .............................................. A61M 5/14
[52] U.S. Cl. ...................... 604/85; 604/132; 604/246; 604/890.1; 128/DIG. 12
[58] Field of Search ...................... 604/83–85, 604/122, 126, 131, 132, 149, 153, 212, 216, 217, 246, 247, 890.1; 128/DIG. 12

[56] References Cited

U.S. PATENT DOCUMENTS

| 4,193,397 | 3/1980 | Tucker et al. | 604/83 X |
|---|---|---|---|
| 4,474,575 | 10/1984 | Eckenhoff et al. | 604/131 |
| 4,668,231 | 5/1987 | de Vries et al. | 604/891 |
| 4,968,301 | 11/1990 | di Palma et al. | 604/132 |
| 4,969,873 | 11/1990 | Steinbach et al. | 604/93 |
| 4,994,031 | 2/1991 | Theeuwes . | |
| 5,024,657 | 6/1991 | Needham et al. . | |
| 5,030,203 | 7/1991 | Wolf, Jr. et al. . | |
| 5,074,844 | 12/1991 | Zdeb et al. . | |

FOREIGN PATENT DOCUMENTS 0059694 1/1982 European Pat. Off. .

Primary Examiner—John D. Yasko
Assistant Examiner—C. Maglione
Attorney, Agent, or Firm—James E. Brunton

[57] ABSTRACT

An apparatus for accurately infusing medicinal agents into an ambulatory patient at specific rates over extended periods of time. The apparatus is of a compact, low profile, laminate construction and includes an elastic distendable membrane, which, in cooperation with a thin planar base, defines a fluid chamber having a fluid outlet. Disposed within the fluid chamber is a thin fluid permeable member which precisely controls the rate of fluid flow through the fluid outlet.

43 Claims, 17 Drawing Sheets

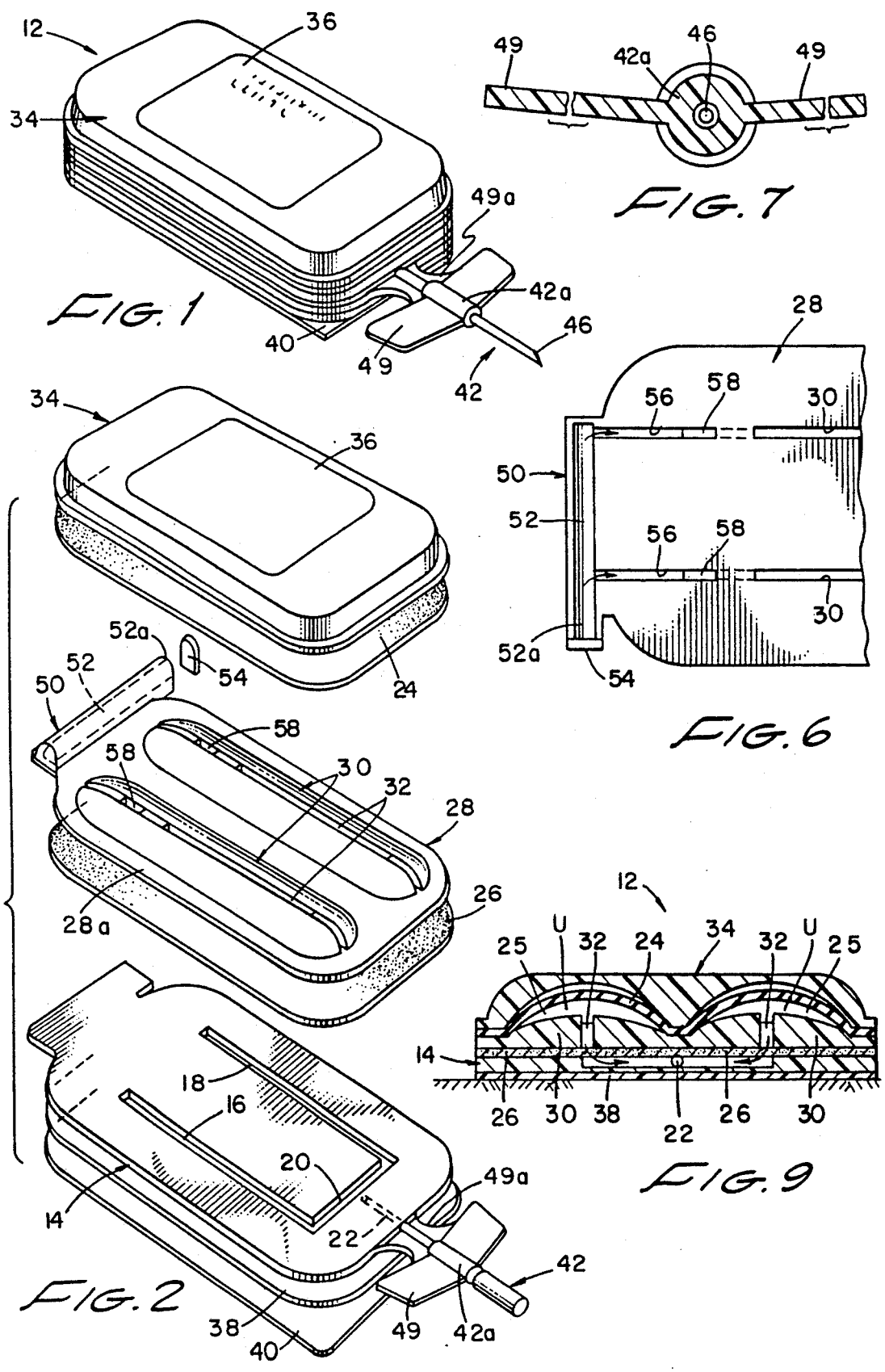

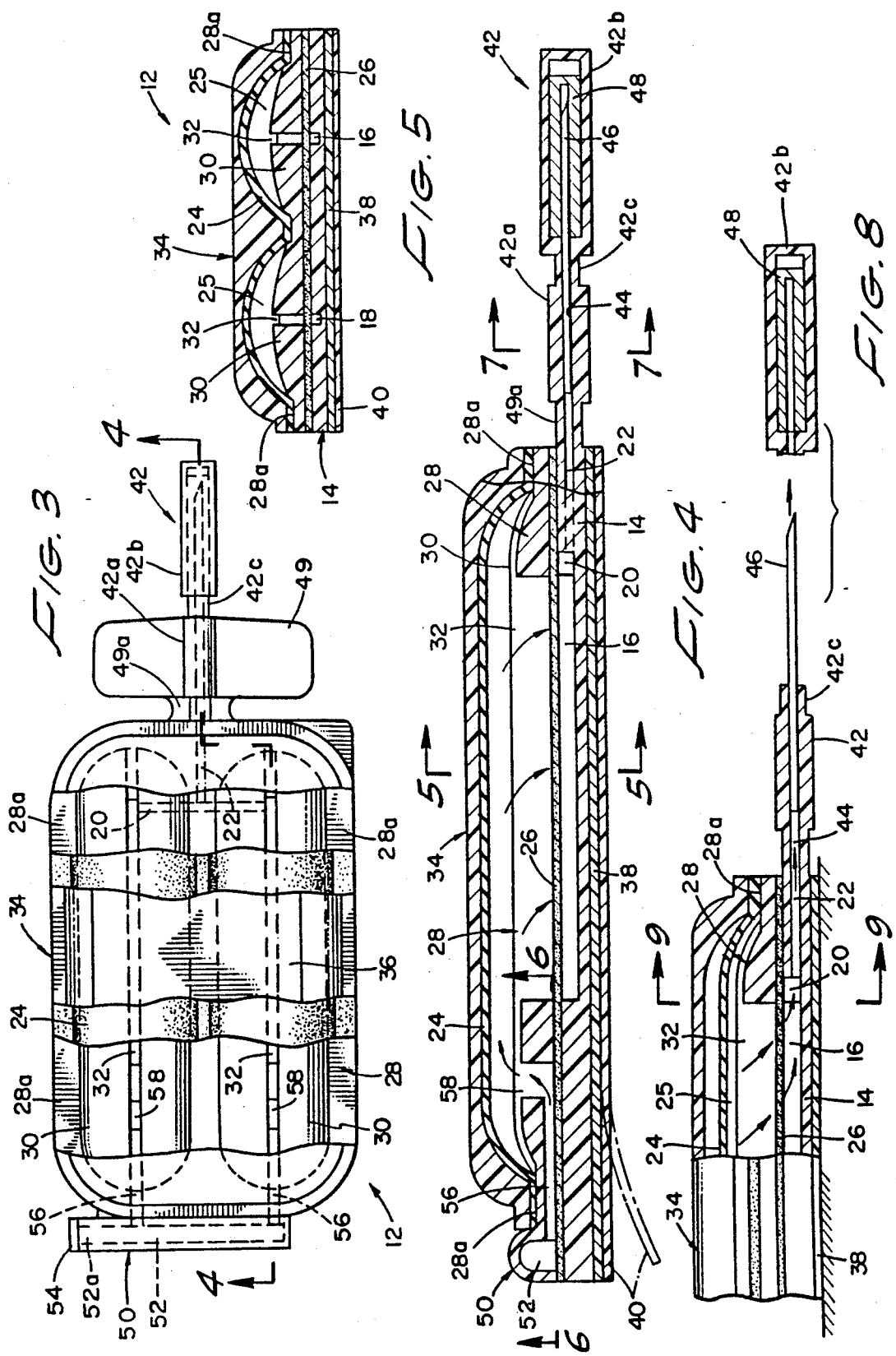

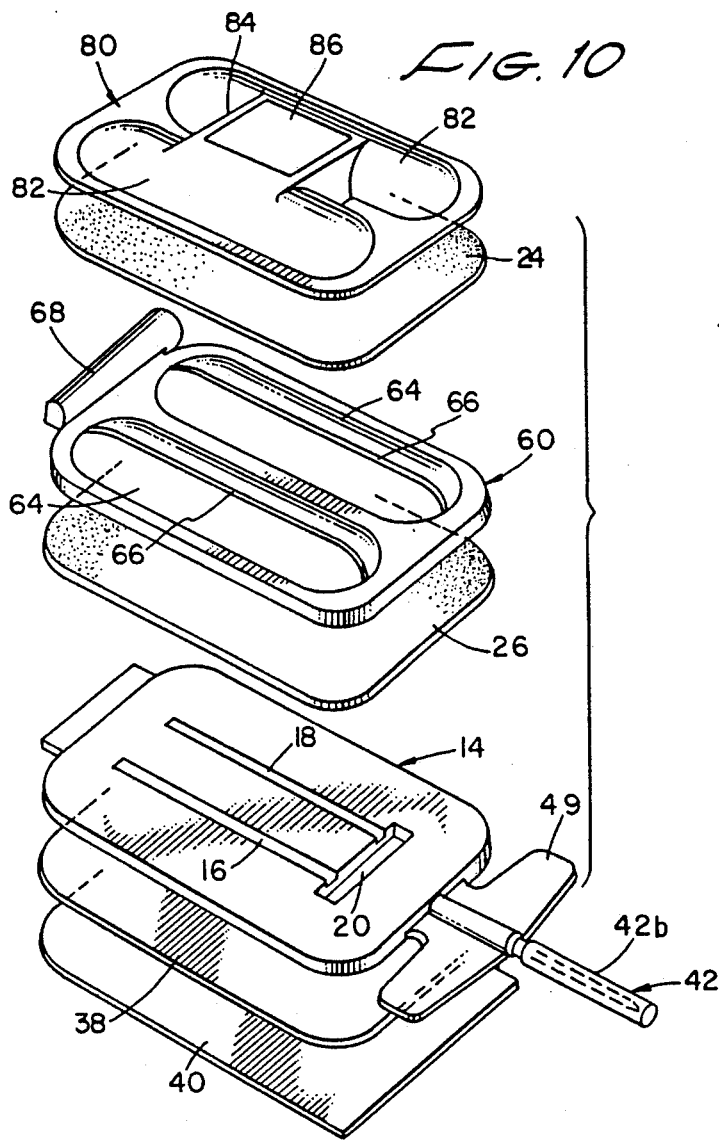
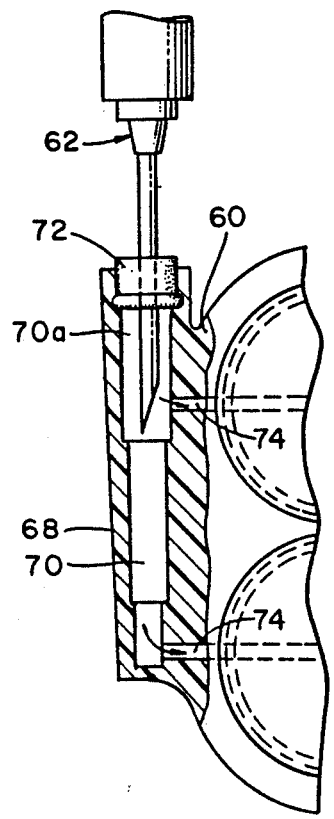
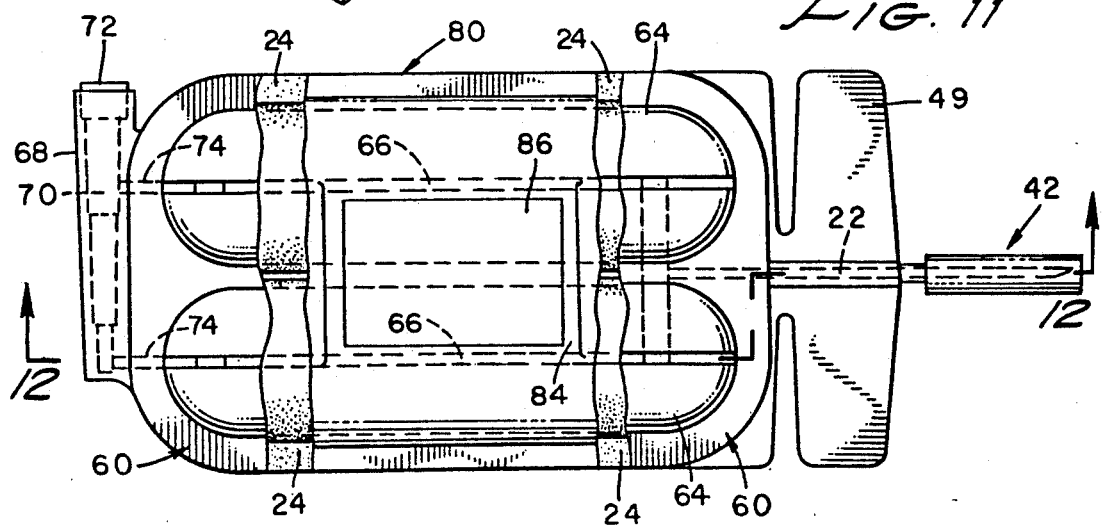

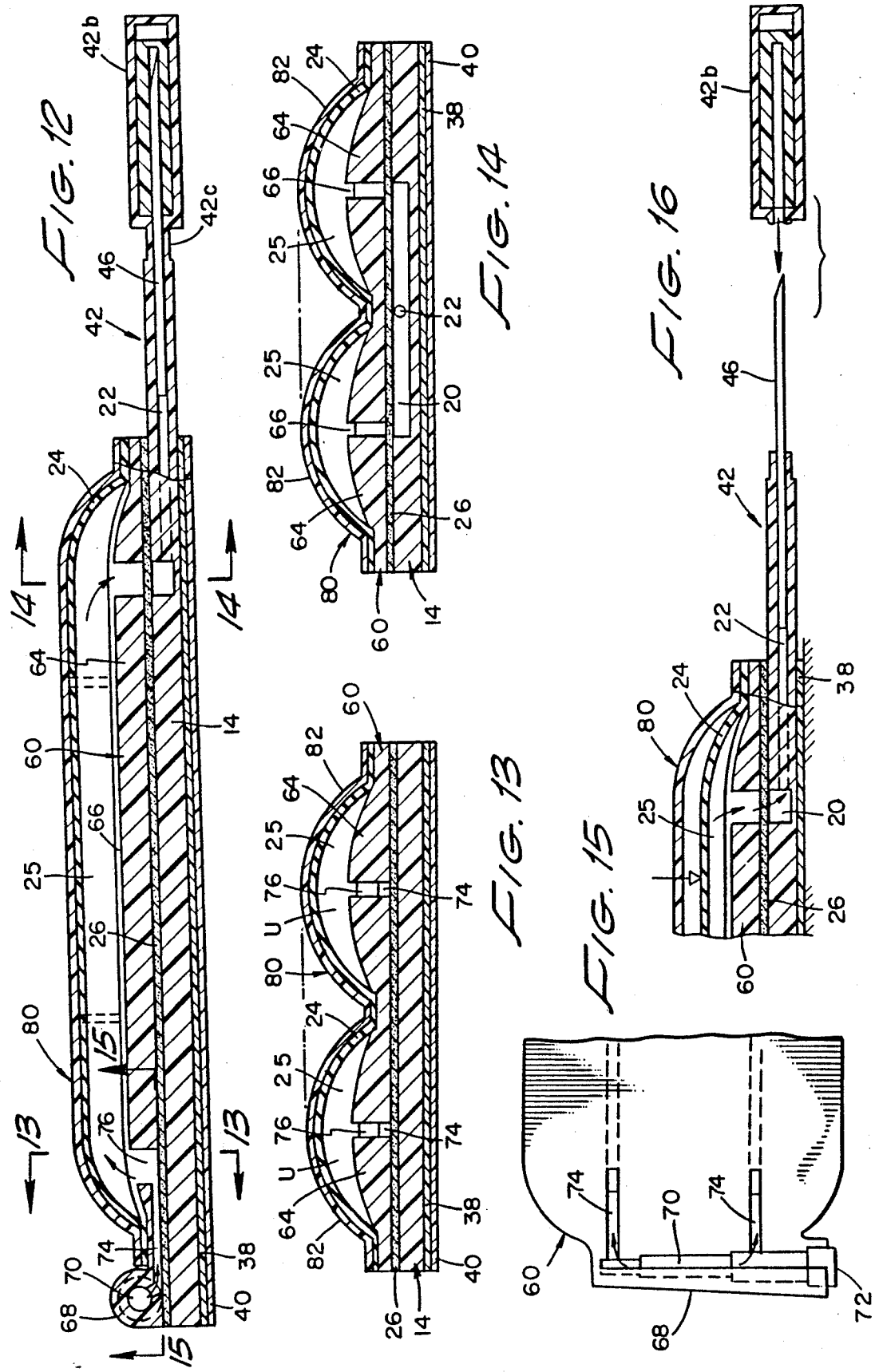

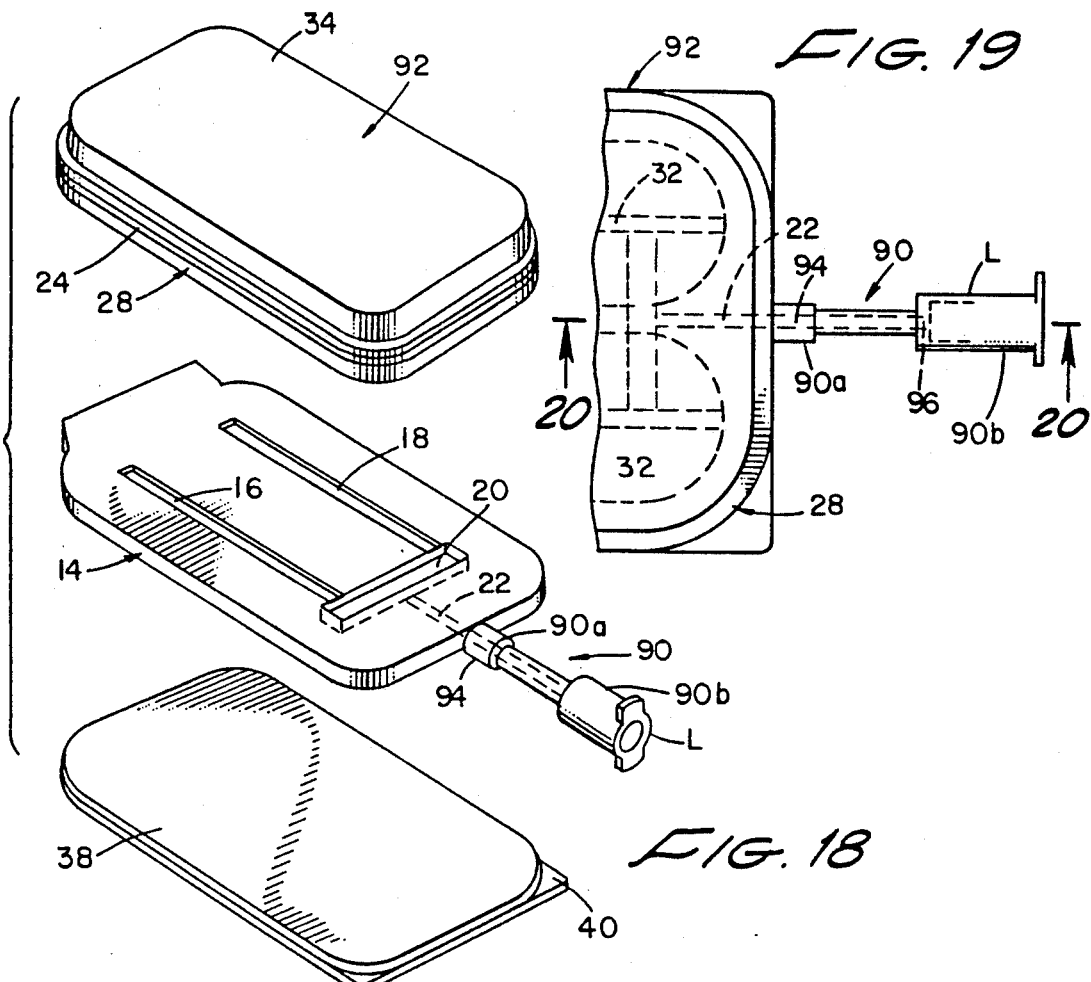
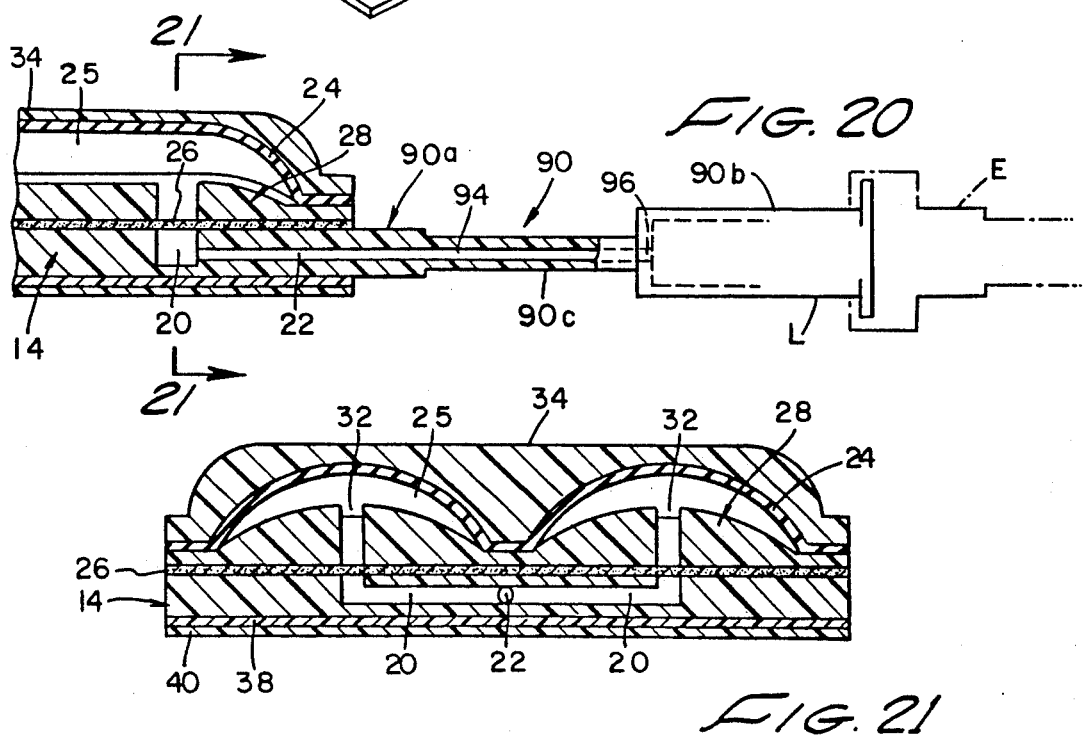

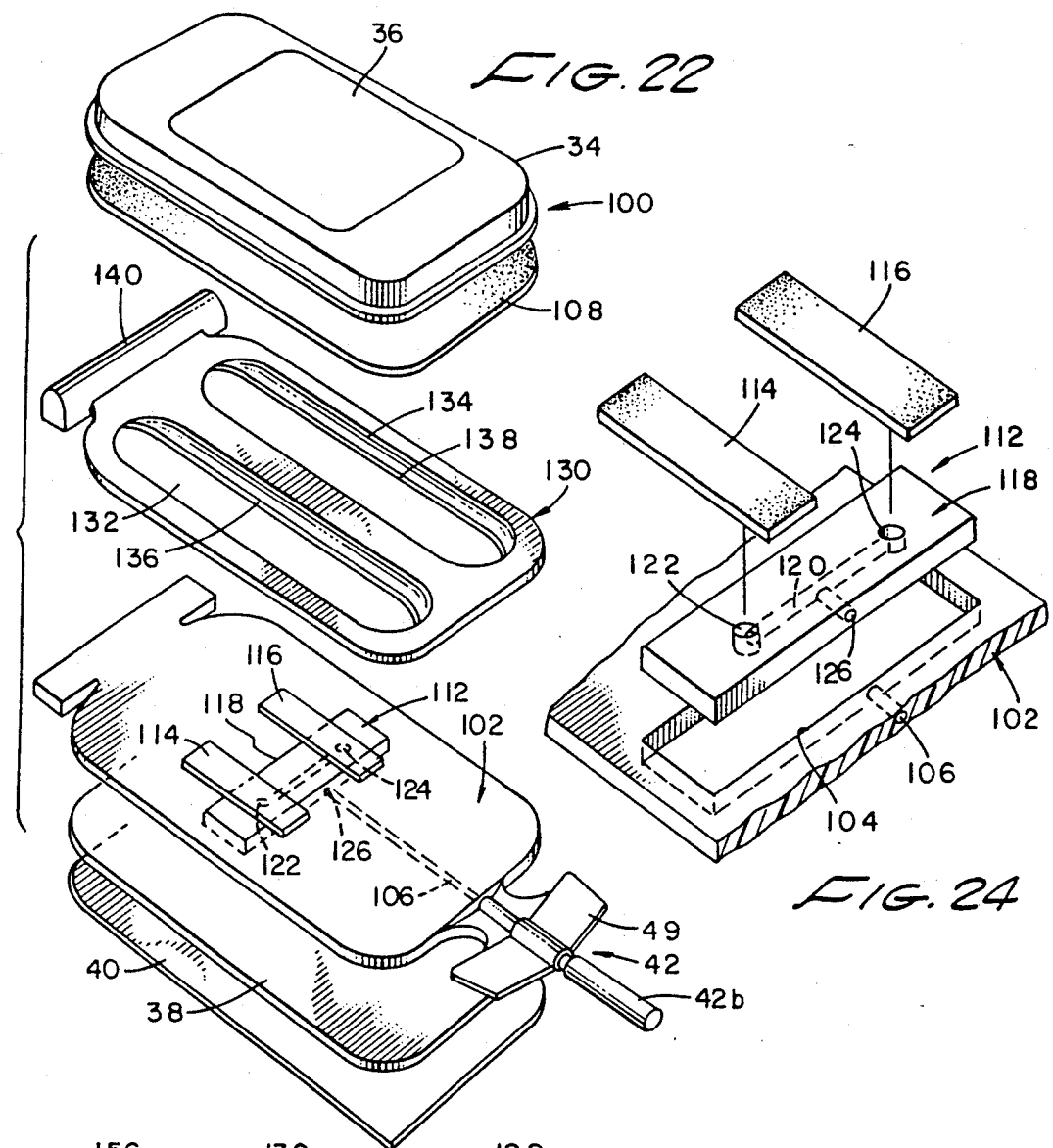
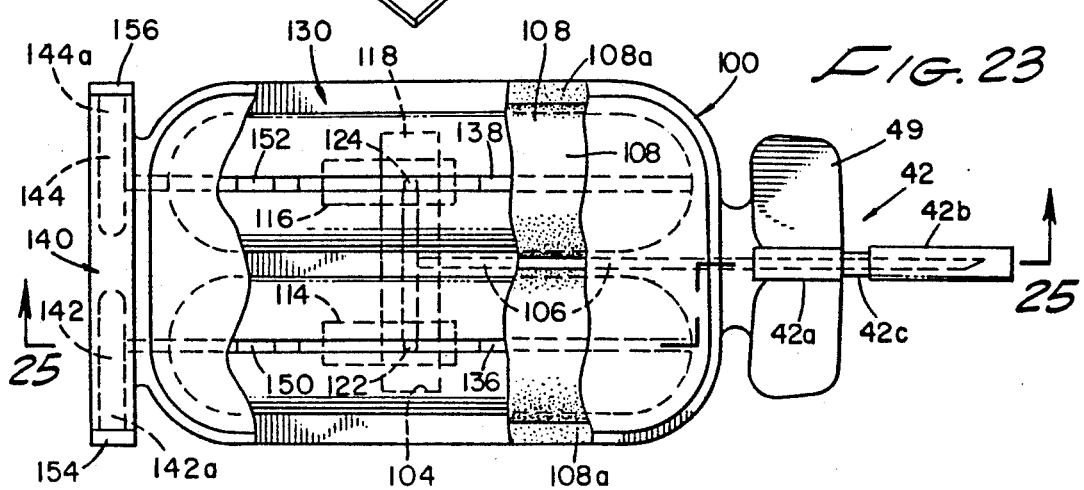

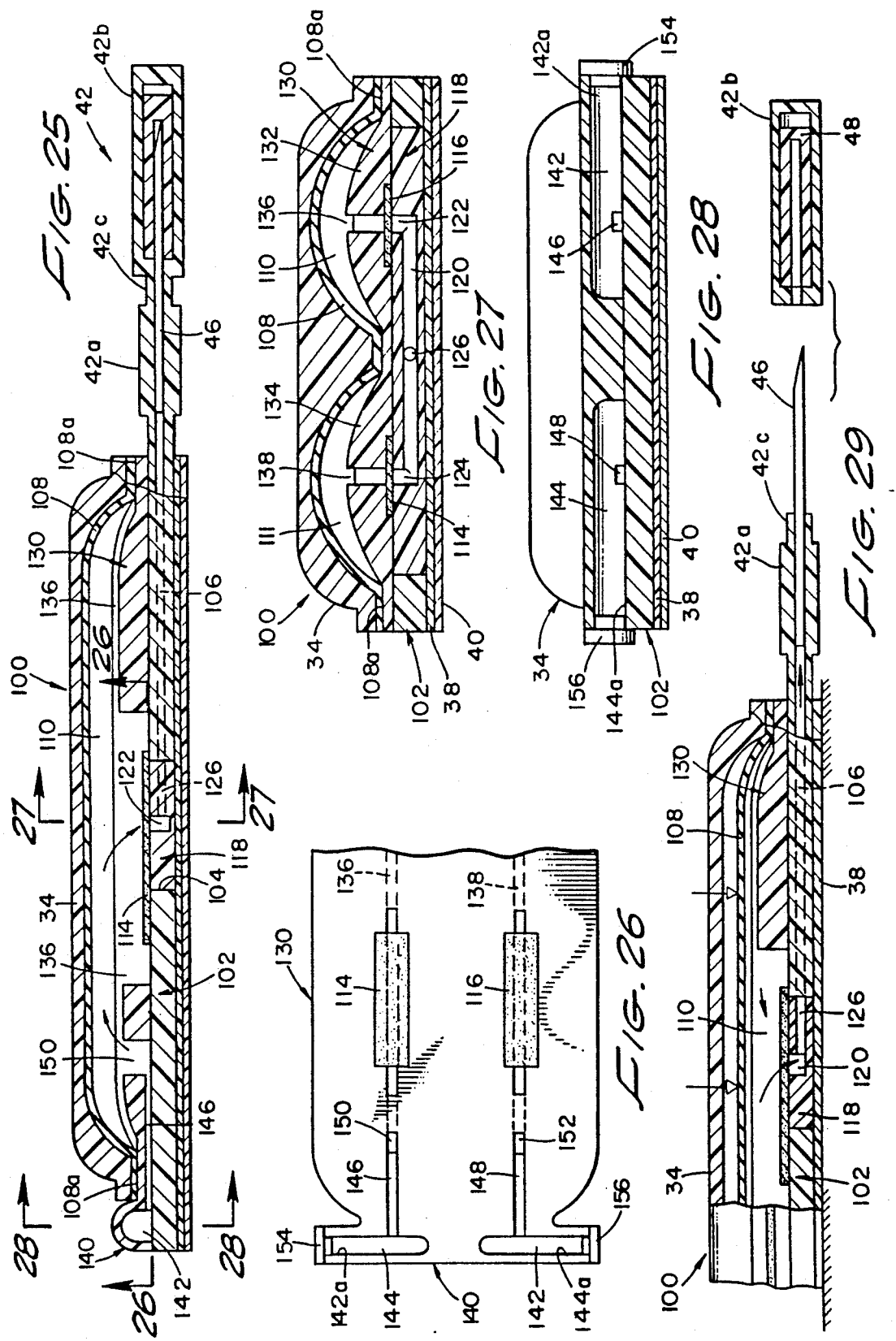

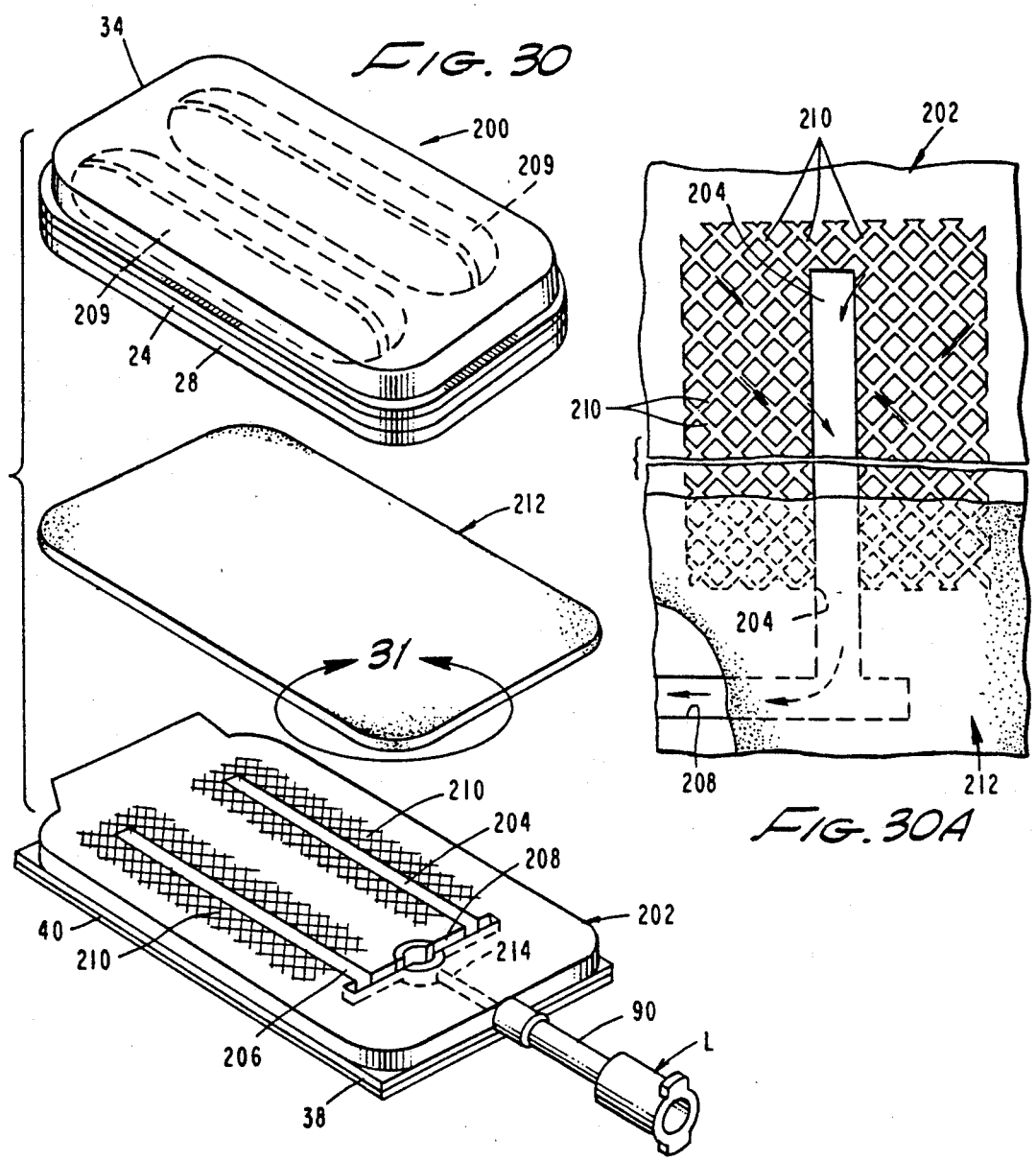
FIG. 30
FIG. 30A
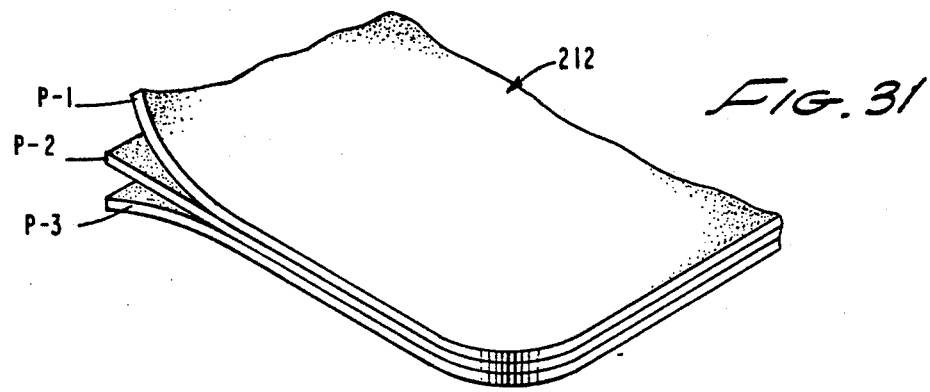
FIG. 31

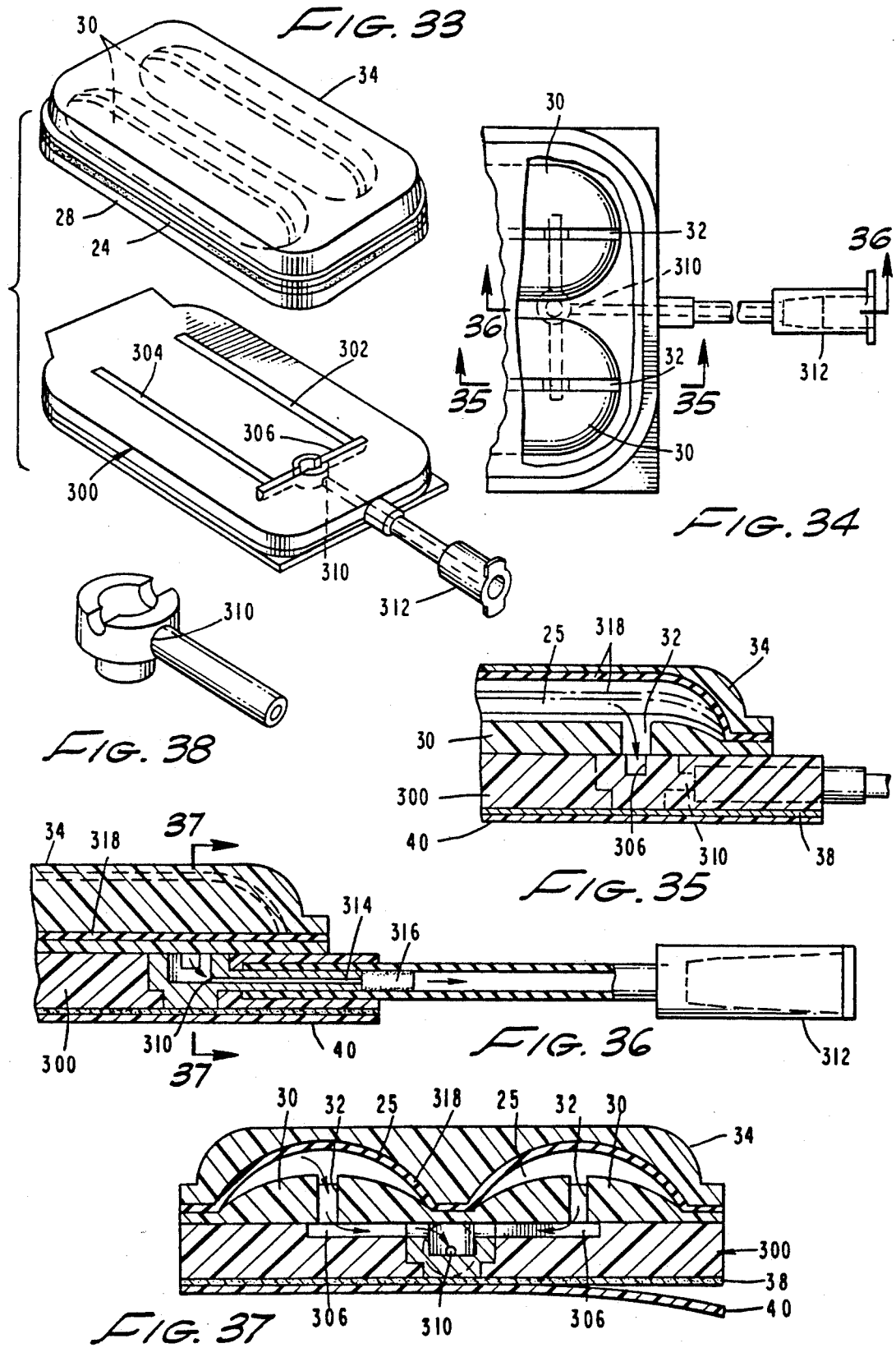

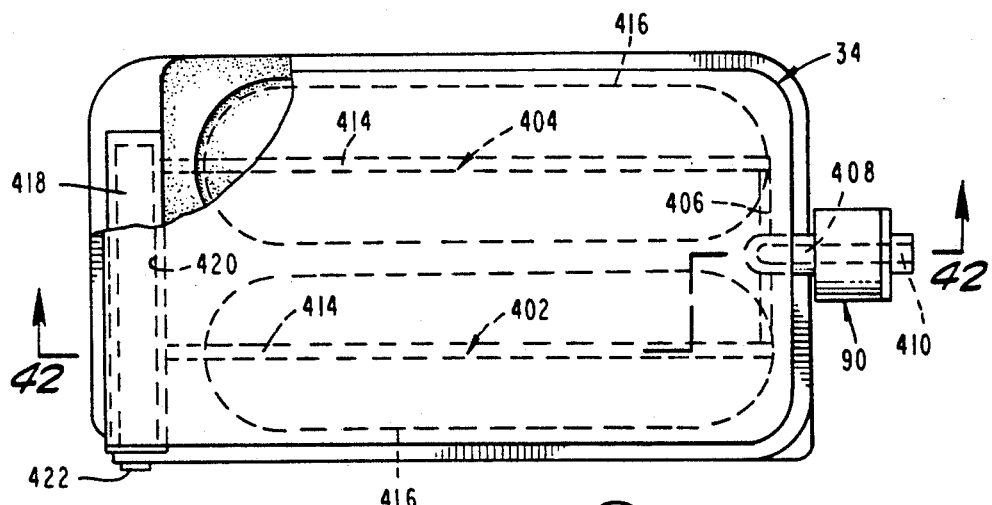
FIG. 40
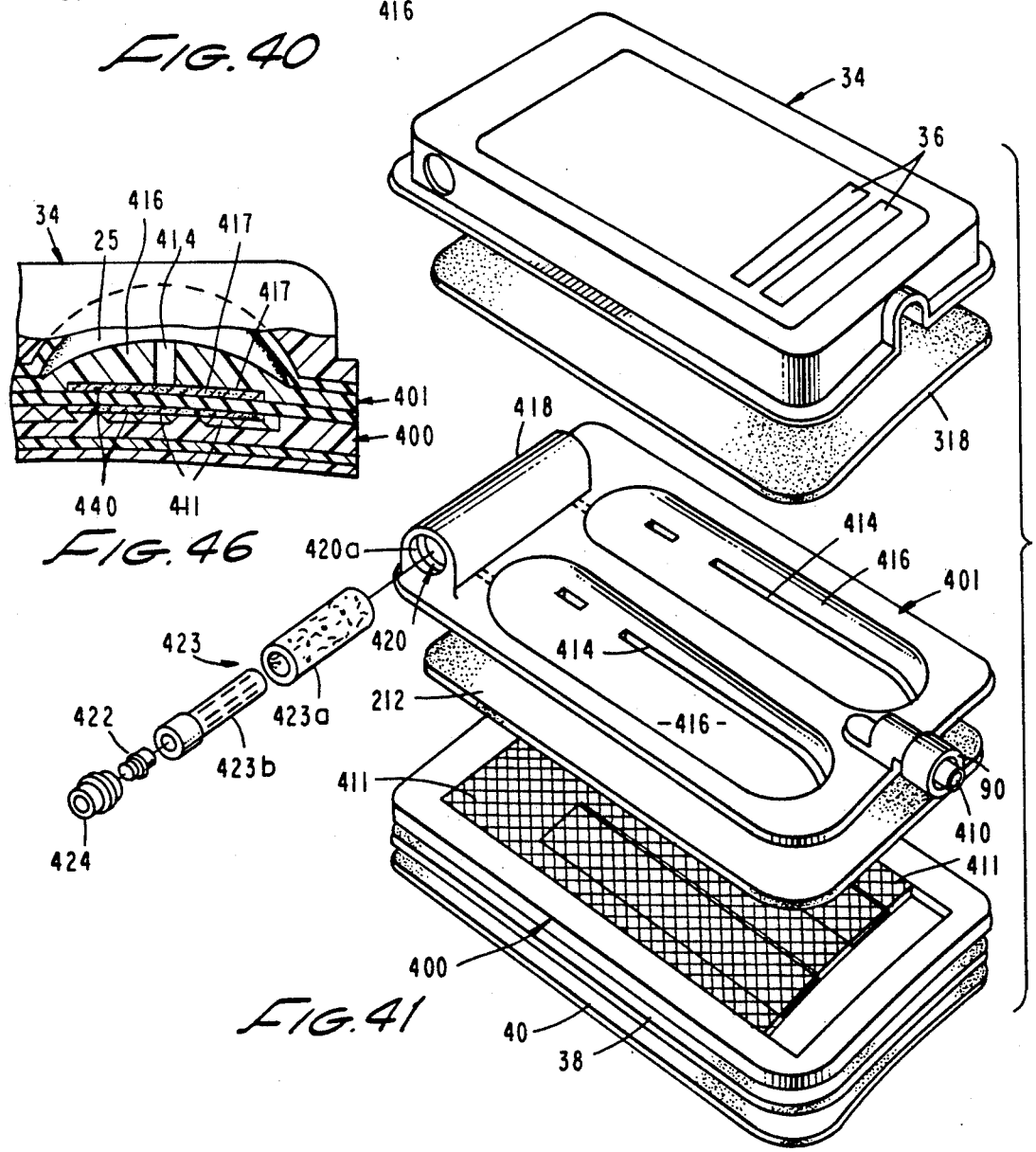
FIG. 46
FIG. 41

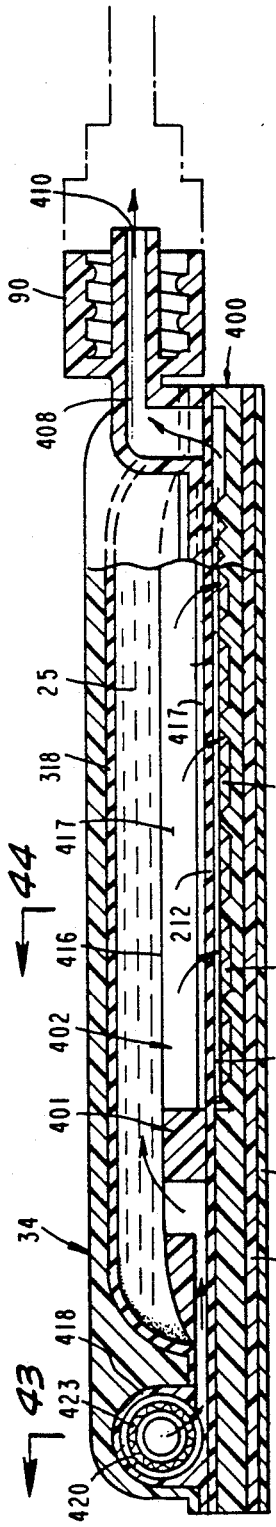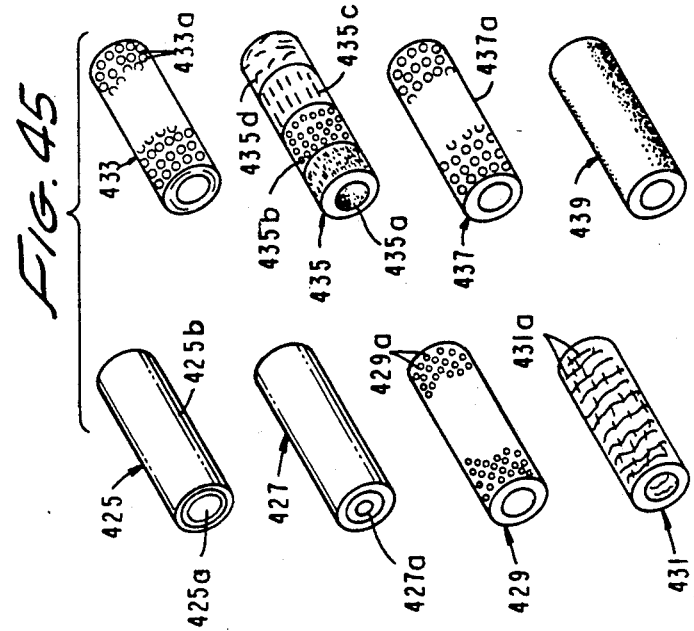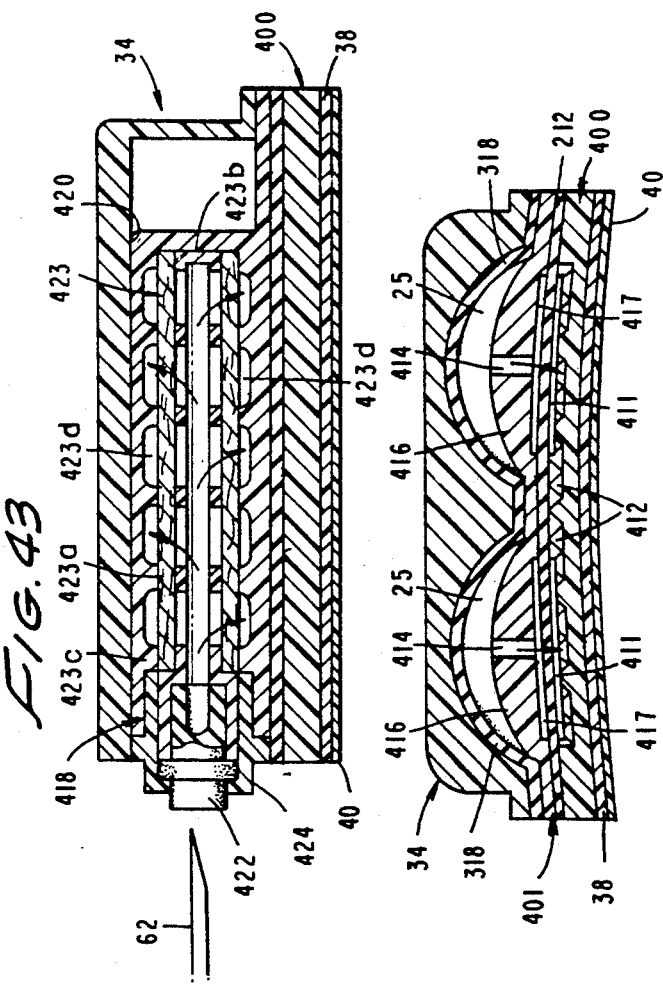

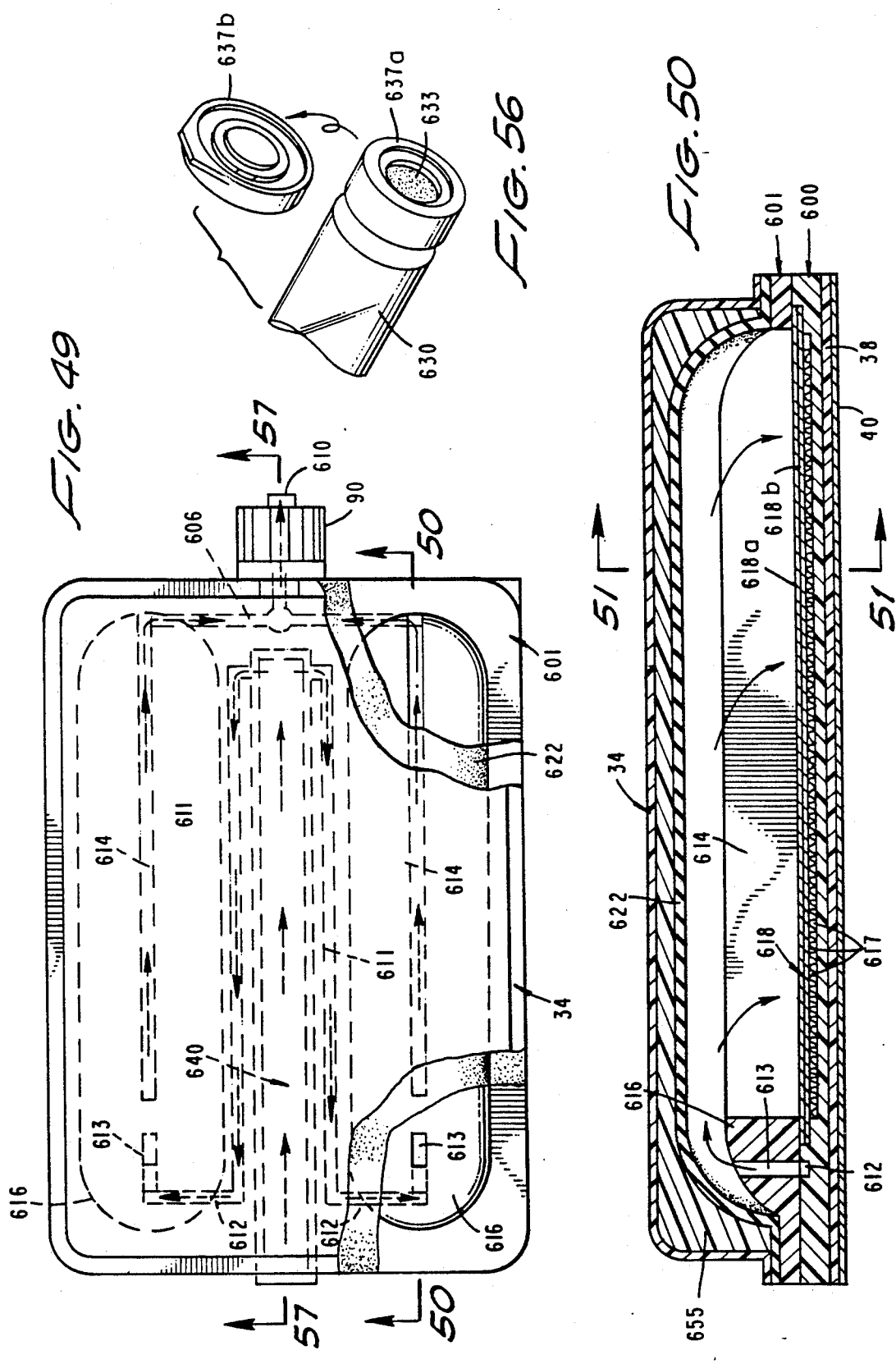

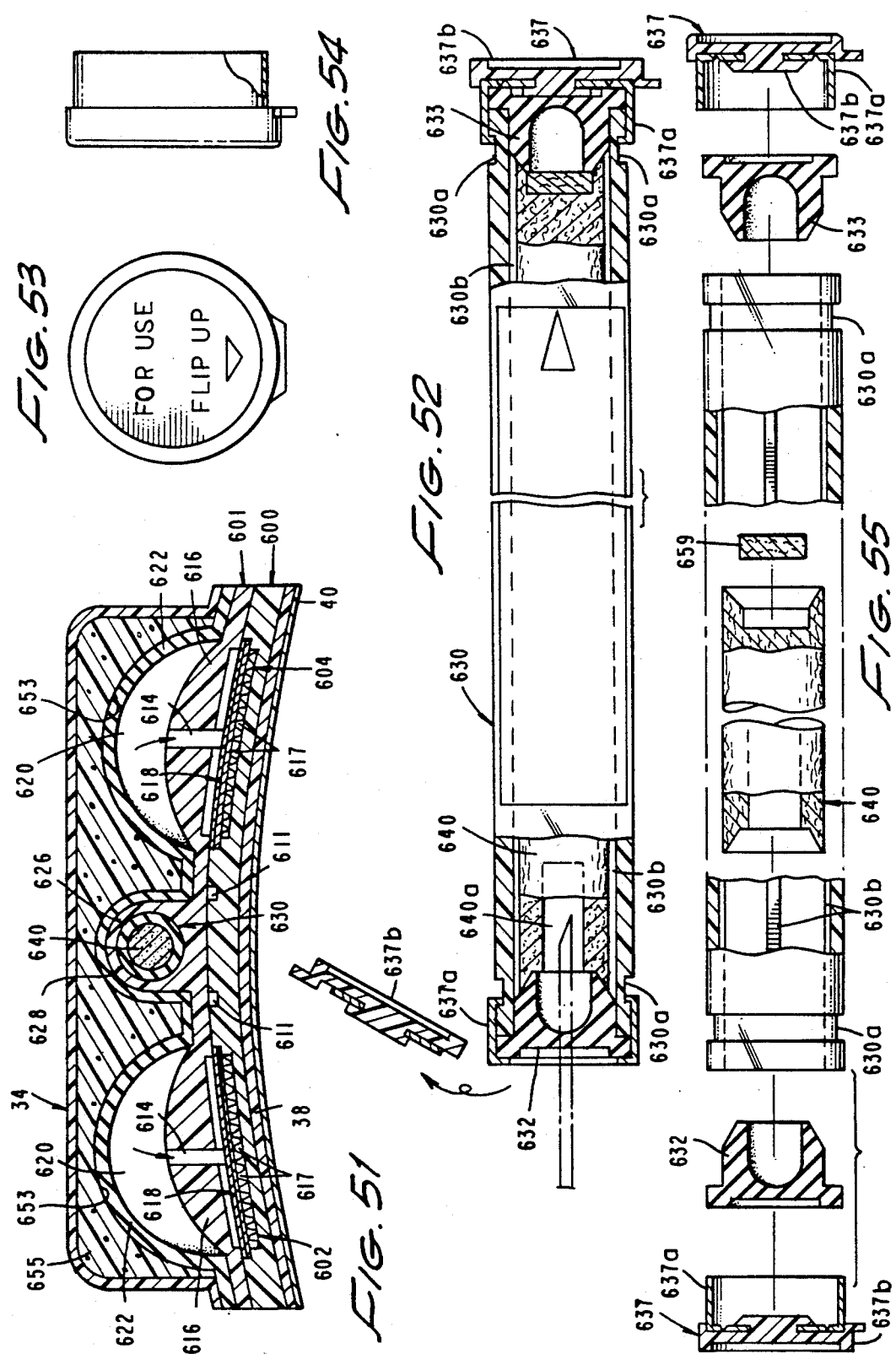

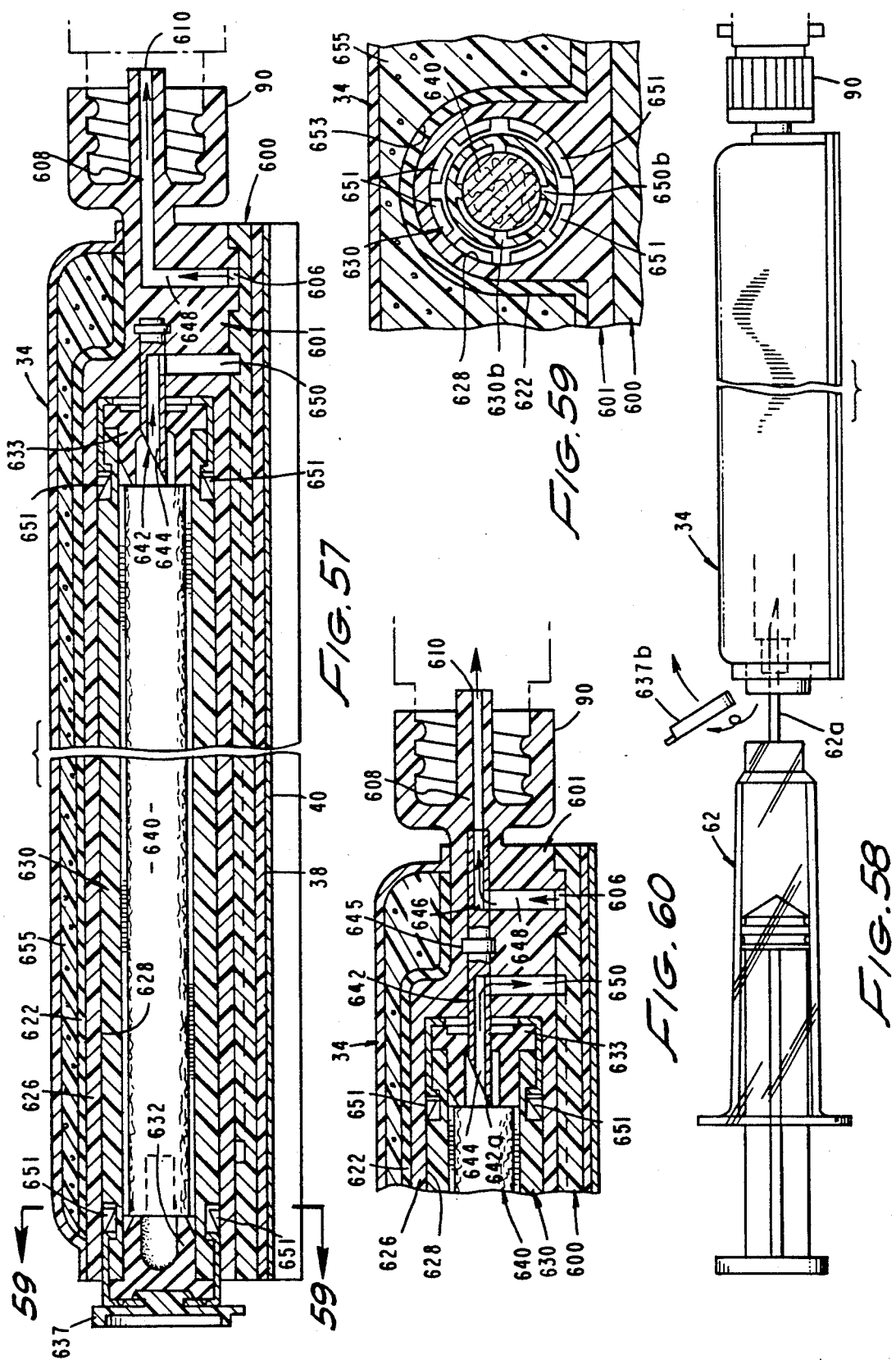

FLUID DELIVERY APPARATUS

This is a continuation application of Ser. No. 07/642,208. filed Jan. 16, 1991, now U.S. Pat. No. 5,169,389, which is a continuation in part of Ser. No. 07/367,304 Filed Jun. 16, 1989 which has now issued to U.S. Pat. No. 5,019,047

BACKGROUND OF THE INVENTION

FIELD OF THE INVENTION

The present invention relates generally to fluid delivery devices. More particularly, the invention concerns an improved apparatus for infusing medicinal agents into an ambulatory patient at specific rates over extended periods of time.

DISCUSSION OF THE INVENTION

Many medicinal agents require an intravenous route for administration thus bypassing the digestive system and precluding degradation by the catalytic enzyme in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldly and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a, plate-like base defines a fluid chamber that contains the fluid which is to be dispensed. The elastomeric film membrane controllably forces fluid within the chamber into fluid flow channels provided in the base. In one form of the apparatus of the invention, a thin, planar shaped flow rate control member is strategically located within the chamber to precisely control the rate of flow of the liquid toward the fluid flow channels. The flow rate control member can be very thin and can be selected to have a very precise degree of permeability so that the rate of flow of fluid into the fluid flow channels can be controlled with great accuracy.

The use of state of the art thin membranes and films permits the construction of compact, low profile, laminated structures which are easy to use and inexpensive to manufacture. When the devices of the invention are to be used with ambulatory patients they are constructed of flexible materials and are provided with a thin adhesive backing which permits the device to be conveniently self-affixed to the patient's arm or other parts of the body.

The apparatus of the invention can be used with minimal professional assistance in an alternate health care environment, such as the home. By way of example, devices of the invention can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus which can be used for the precise infusion of pharmaceutical fluids to an ambulatory patient at controlled rates over extended periods of time.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use.

Another object of the invention is to provide an infusion device in which fluids can be delivered either at a fixed rate or at variable rates and one which is operational in all altitudes and attitudes.

Still another object of the invention is to provide an apparatus of the class described which is soft, conformable and compliant so as to readily conform to the patient's anatomy proximate the point of infusion.

Yet another object of the invention is to provide an apparatus as described in the preceding paragraph which is provided with a thin, flexible foam backing with adhesive for self-attachment. The apparatus can be unobtrusively worn under clothing.

A further object of the invention is to provide a low profile, fluid delivery device of laminate construction which can be manufactured inexpensively in large volume by automated machinery.

Another object of the invention is to provide a device of the character described in which fluid is dispelled from the apparatus through either an integral infusion needle, or through a luer type connector, by a thin, distendable membrane cooperatively associated with a thin, plate-like base.

Another object of the invention is to provide an apparatus of the aforementioned character in which the distendable member is permeable to gases at least in one direction, whereby gases within the medicinal agent can be released from the fluid chamber and not injected into the patient.

Still another object of the invention is to provide an apparatus as described in the preceding paragraphs in which the rate of fluid flow from the apparatus is precisely controlled by a thin planar shaped, fluid permeable member which forms a part of the low profile, laminate construction of the apparatus.

Another object of the invention is to provide a fluid delivery device embodying an iostropic distendable membrane with a uniform modulus of elasticity which cooperates with a base to define a fluid chamber having a fluid outlet in communication with dispensing port for dispensing fluid from the device and including a flow control element disposed intermediate the fluid outlet and the dispensing port.

Still another object of the invention is to provide a device as described in the preceding paragraph in which the flow control element comprises a restriction which controllably restricts the flow of fluid between the fluid outlet and the dispensing port.

A further object of the invention is to provide a fluid delivery device embodying a distendable membrane assembly which cooperates with a base to define a fluid chamber having a fluid outlet in which the distendable membrane assembly is of multilaminate construction being made up of a plurality of individual members or layers which cooperate to controllably urge fluid within the fluid chamber outwardly of the fluid outlet of the device.

Another object of the invention is to provide a fluid delivery device of the chamber described in the preceding paragraph which includes a rate control membrane and in which the base is provided with a multiplicity of micro-channels for conducting fluid to the rate control membrane at precise rate over a predetermined active area.

A principal object of one form of the invention is to provide a novel agent formulation dispenser adopted for use with a slightly modified version of the basic fluid delivery device of the present invention for administering an aqueous solution containing selected drugs or other chemical compounds at a controlled rate.

BRIEF DESCRIPTION OF THE DRAWINGS

FIG. 1 is a generally perspective view of one form of the fluid dispensing apparatus of the invention.

FIG. 2 is an exploded, generally perspective view of the apparatus of FIG. 1.

FIG. 3 is a top view of the apparatus partly broken away to show internal construction.

FIG. 4 is an enlarged cross sectional view taken along lines 4—4 of FIG. 3.

FIG. 5 is a cross sectional view taken along lines 5—5 of FIG. 4.

FIG. 6 is a fragmentary view taken along lines 6—6 of FIG. 4.

FIG. 7 is a cross sectional view taken along lines 7—7 of FIG. 4.

FIG. 8 is a view similar to FIG. 4, but illustrating the separation of the molded needle cover from the device.

FIG. 9 is a cross sectional view taken along lines 9—9 of FIG. 8.

FIG. 10 is a generally perspective exploded view of another embodiment of the fluid dispensing apparatus of the present invention.

FIG. 11 is a top view of the apparatus shown in FIG. 10.

FIG. 12 is a cross sectional view taken along lines 12—12 of FIG. 11.

FIG. 13 is a cross sectional view taken along lines 13—13 of FIG. 12.

FIG. 14 is a cross sectional view taken along lines 14—14 of FIG. 12.

FIG. 15 is a fragmentary view taken along lines 15—15 of FIG. 12.

FIG. 16 is a view similar to FIG. 12, but showing the molded needle cover separated from the device.

FIG. 17 is a greatly enlarged fragmentary view illustrating the method of fluid fill of the apparatus of this form of the invention.

FIG. 18 is a generally perspective exploded view of another embodiment of the apparatus of the present invention.

FIG. 19 is a fragmentary top view of the apparatus of this form of the invention.

FIG. 20 is a cross sectional view taken along lines 20—20 of FIG. 19

FIG. 21 is a cross sectional view taken along lines 20—20 of FIG. 19.

FIG. 22 is a generally perspective exploded view of still another form of the apparatus of the present invention.

FIG. 23 is a plan view of the apparatus of FIG. 22 partly broken away to show internal construction.

FIG. 24 is a greatly enlarged fragmentary perspective view of a portion of the apparatus illustrating the arrangement of the rate control membranes of the device.

FIG. 25 is a cross sectional view taken along lines 25—25 of FIG. 23.

FIG. 26 is a fragmentary view taken along lines 26—26 of FIG. 25.

FIG. 27 is a cross sectional view taken along lines 27—27 of FIG. 25.

FIG. 28 is a cross sectional view taken along lines 28—28 of FIG. 25.

FIG. 29 is a fragmentary, cross sectional view similar to FIG. 25, but showing the needle cover separated from the apparatus of the invention.

FIG. 30 is a generally prospective, exploded view of still another embodiment of the present invention.

FIG. 30A is a fragmentary plan view taken along lines 30A—30A of FIG. 32 showing the internal construction of the apparatus of FIG. 30.

FIG. 31 is a fragmentary, generally perspective view of the circled portion of the flow rate control membrane as shown in FIG. 30.

FIG. 33 is an exploded, generally perspective view of still another form the apparatus of the invention.

FIG. 34 is a fragmentary plan view of the fluid outlet portion of the apparatus of FIG. 33, partly broken away to show internal construction.

FIG. 35 is a cross-sectional view taken along lines 35—35 of FIG. 34.

FIG. 36 is a cross-sectional view taken along lines 36—36 of FIG. 34.

FIG. 37 is a cross-sectional view taken along lines 37—37 of FIG. 36.

FIG. 38 is a fragmentary, generally perspective view of a portion of the flow control means of this form of the apparatus of the invention.

FIG. 40 is a plan view of yet another form of the invention, partly broken away to show internal construction.

FIG. 41 is an exploded, generally perspective view of the form of the apparatus of the invention shown in FIG. 40.

FIG. 42 is a cross-sectional view taken along lines 42—42 of FIG. 40.

FIG. 43 is a cross-sectional view taken along lines 43—43 of FIG. 42.

FIG. 44 is a cross-sectional view taken along lines 44—44 of FIG. 42.

FIG. 45 is a generally perspective view of various forms of activating members for activating the parenteral fluid with a medicament which are usable with this embodiment of the apparatus of the invention.

FIG. 46 is a fragmentary, cross-sectional view similar to FIG. 44 illustrating the use of flow distribution materials within the liquid flow manifolds of the device.

FIG. 49 is a plan view of the apparatus partially broken away to show internal construction.

FIG. 50 is a cross-sectional view taken along lines 50—50 of FIG. 49.

FIG. 51 is a cross-sectional view taken along lines 51—51 of FIG. 50.

FIG. 52 is an enlarged side elevational view partly in cross-section to show internal construction of a additive carrying subassembly of the invention.

FIG. 53 is an enlarged end view of one end cap of the additive subassembly shown in FIG. 52.

FIG. 54 is a side elevational view partly broken away of the end cap shown in FIG. 53.

FIG. 55 is an exploded view of the additive subassembly shown in FIG. 52 partly in cross-section to better illustrate the construction of the subassembly.

FIG. 56 is a fragmentary, generally perspective view of one of the end caps of the additive subassembly of the apparatus.

FIG. 57 is an enlarged, cross-sectional view taken along lines 57—57 of FIG. 50.

FIG. 58 is a side elevational view of the apparatus of this form of the invention being filled by a hypodermic syringe of standard construction.

FIG. 59 is a fragmentary, side elevational view similar to FIG. 57 showing the fluid flow path of the fluid flowing through the apparatus and outwardly toward the dispensing means.

FIG. 60 is a cross-sectional view taken along lines 60—60 of FIG. 57.

DESCRIPTION OF THE INVENTION

Figure 32:
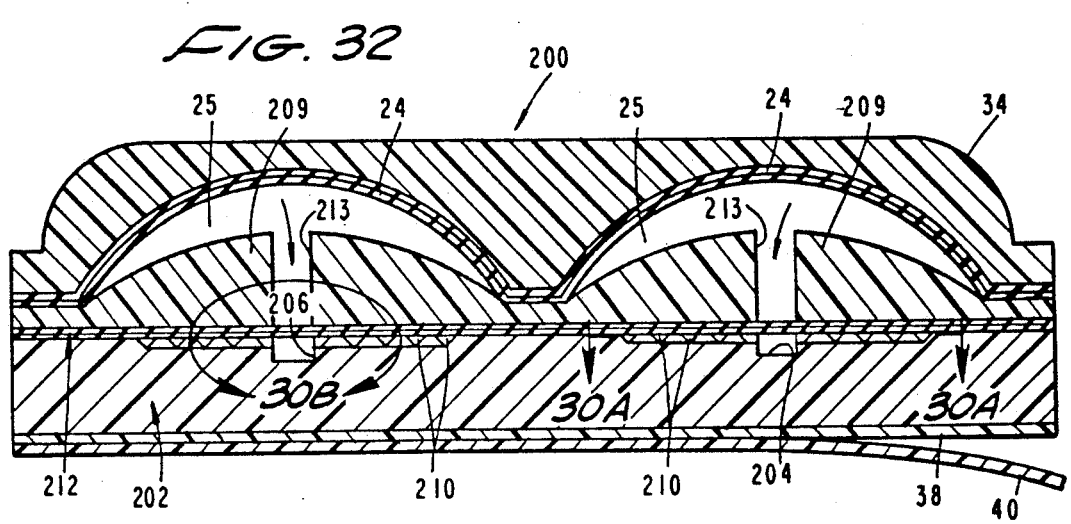
FIG. 32 is a cross-sectional view of the apparatus shown in FIG. 30.

Referring to the drawings and particularly to FIGS. 1 through 9, one embodiment of the apparatus for use in infusing medicinal fluids into a patient is there illustrated and generally designated by the numeral 12. As indicated in FIG. 1, the apparatus of this form of the invention comprises a laminate, or layered, structure made up of a plurality of thin plate-like components. As best seen by referring to FIG. 2, the apparatus comprises a thin, generally planar plate-like base 14, having a pair of flow rate control channels provided here as longitudinally extending fluid conduits 16 and 18. Conduits 16 and 18 are interconnected by a fluid transfer manifold, or transverse conduit 20, which, in turn, is interconnected with a fluid outlet passageway 22. A thin, generally planar distendable elastomeric membrane, or member, 24 cooperates with base 14 to form a chamber 25 (FIG. 4). Member 24 is distendable out of plane in the manner shown in FIG. 4 by the introduction of fluid into the chamber under pressure. As the distendable member 24 is distended by the fluid pressure, internal stresses are formed in the member which continuously urge it to return to its original planar configuration. The method of introduction of fluids into chamber 25 will presently be described. As shown in FIG. 5, to maintain the low profile character of the device, the height of the fluid chamber is substantially less than the width of base 14.

Forming an important aspect of the apparatus of the invention is the provision of flow control means which is disposed internally of chamber 25 for controlling the rate of fluid flow through the outlet 22 formed in base member 14. In the embodiment of the invention here-shown, the flow control means is provided in the form of a thin, permeable member 26 which is superimposed over base 14 in the manner shown in FIG. 4. As will presently be described, member 26 precisely controls the rate of fluid flow from chamber 25 into fluid conduits 16, 18 and 20 formed in base 14. It is this precise control of the rate of fluid flow which enables infusion into the patient of medicinal fluids at an extremely precise rate over extended periods of time ranging from several hours to in excess of 24 hours depending on sized reservoir volume.

Superimposed over flow control member 26 is a distendable membrane engagement means. This means is here provided in the form of a generally planar member 28 having a peripheral portion 28a to which the margins of distendable member 24 are bonded, as by adhesive or thermo-bonding. Member 28 also has a pair of longitudinally extending, spaced apart upstanding protruberances 30. Each of the protruberances 30 is provided with a longitudinally extending first fluid passageway or conduit 32. When the apparatus is assembled in the manner shown in FIG. 9, passageways 32 are superimposed over fluid conduits 16 and 18 and protruberances 30 extend upwardly into fluid chamber 26 so as to define ullage "U" within chamber 25. In operation of the device, as distendable membrane 24 attempts to return to its original planar configuration (FIG. 9), it will move toward engagement with the upper surfaces of protruberances 30 and in so doing will efficiently force the fluid contained within chamber 25 uniformly through the flow control member 26 and into passageways 16 and 18. The configuration of protuberances 30 ensure that all of the fluid within chamber 25 will be dispelled therefrom as the membrane returns toward its starting configuration. Passageways 16, 18, and 32 can be alternately configured to provide various degrees of fluid exposure to rate control membrane 26 whereby the active surface area of membrane 26 is increased or decreased.

Superimposed over the assembly comprising base 14, distendable membrane 24, flow control member 26, and distendable membrane engaging member 28 is a porous plastic cover 34 which functions to provide a superstructure and a venting means for venting gases, if any, contained within the medicinal agent. Affixed to the top of cover 34 is a medicant and use instruction label 36 which can be used to identify the medicinal fluid contained within chamber 25 of the device.

Affixed to the bottom of base 14 is a cushioning means shown here as a thin, planar shaped foam pad 38. Foam pad 38 is provided with adhesive on both its upper and lower surfaces. The adhesive on the upper surface of pad 38 enables the pad to be affixed to the lower surface of base 14. As indicated in FIGS. 2 and 4, a peel strip 40 is connected to the bottom surface of foam pad 38 by the adhesive provided thereon. When the device is to be used, peel strip 40 can be stripped away from pad 38 so that the adhesive on the lower surface of the foam pad 38 can be used to releasably affix the apparatus of the invention to the anatomy of the patient.

Turning now to FIGS. 4 and 8, a needle assembly 42 is integrally formed with base 14. Needle assembly 42 which includes a distal portion 42a and a proximal portion 42b, is provided with a longitudinally extending bore 44. As best seen in FIG. 4, bore 44 is in communication with outlet passageway 22 formed in base 14. Fixedly received within that portion of passageway 44, which extends through distal portion 42a, is a hollow infusion needle 46 of the character typically used for injecting fluids into a patient. The fluid outlet end of needle 46 is received within that portion of passageway 44 which extends through proximal portion 42b. Intermediate portions 42a and 42b is a reduced diameter frangible portion 42c which can be broken so as to separate portions 42a and 42b to expose the outlet end of needle 46 in the manner shown in FIG. 8. Also forming a part of proximal portion 42b is a protective sheath 48 for encapsulating and protecting needle 46. Needle assembly 42 also includes web means for further assisting in securing and maintaining the needle in an appropriate invasive position to preclude inter-vascular trauma. The web means are here provided as a soft, flexible butterfly assemblage 49, which, as shown in FIGS. 1 and 7, is integrally formed with base 14 and joined therewith by webbing 49a. Butterfly assembly 49 also provides appropriate surface area for tape adhesion covering the injection site.

Turning now to FIGS. 2, 3, 4 and 6, the distendable membrane engagement element 28 which comprises the means for creating an ullage within chamber 25, also includes an upstanding transversely extending portion 50 having a fluid passageway 52 extending therethrough. In the present embodiment of the invention, the open end 52a of passageway 52 is closed by a closure member 54 which is adapted to sealably close passageway 52 after chamber 25 has been filled with the selected medicinal agent. Passageway 52 can also be closed by any suitable means such as thermal or mechanical sealing. As best seen by referring to FIG. 4, passageway 52 is in communication with a pair of longitudinally extending passageways 56 formed in element 28. Passageways 56 are, in turn, in communication with chamber 25 via passageways 58. As illustrated in FIG. 2, passageways 58 extend through protuberances 30 and are disposed in the ends of protuberances 30 located proximate transversely extending passageway 52.

The apparatus of this first embodiment of the invention is adapted to be filled with the selected medicinal fluid at time of manufacture. This is accomplished by removal of plug 54 so that fluid under pressure can be forced into passageway 52 and thence into chamber 25 via passageways 56 and 58. As the fluid under pressure flows through passageways 58, it will cause the membrane 24 to distend upwardly into initial engagement with cover 34 in the manner shown in FIG. 4. After chamber 25 has been filled with the medicinal fluid, closure plug 54 is bonded or otherwise affixed in place within the open end 52a of conduit 52 so as to seal chamber 25 with respect to atmosphere.

So long as needle assembly 42 remains intact in the manner shown in FIG. 4, the fluid will be retained within chamber 25. However, upon twisting and breaking the frangible section 42c so that portion 42b of the needle assembly can be removed as shown in FIG. 8, distendable membrane 24 will begin to expel fluid through the needle 46. The rate of expulsion of fluid is, of course, controlled by the permeable membrane 26 which is disposed intermediate the fluid flow passageways 32 of member 28 and fluid flow passageways 16 and 18 formed in base 14.

As previously mentioned, the state of the art materials used in the construction of the apparatus of the invention markedly contribute to the reliability, accuracy and manufacturability of the apparatus. Before discussing the alternate forms of the invention shown in the drawings, a brief review of the materials used in constructing the apparatus is in order.

With respect to the base 14, a wide variety of materials can be used, including; metals, rubber or plastics that are compatible with the liquids they contact and are preferably not non-allergenic. Examples of such materials are stainless steel, aluminum, latex rubber, butyl rubber, nitrile rubber, polyisiprene, styrene-butadiene copolymer, silicones, polyolefins such as polypropylene and polyethylene, polyesters, polyurethane, polyamides and polycarbonates. Manufacturers of suitable materials include; Dow Corning of Midland, Mich., General Electric of Schenectady, N.Y. and Shell Chemical Company of Houston, Tex., DuPont Chemical of Wilmington, Del., and Eastman Chemical of Kingsport, Tenn.

Considering next the important flow control means, or member 26, precision microflow through this important component is a pressure driven flow delivery process with controllable delivery rates between 0.1 to 4.5 milliliters per hour. Depending on the medicinal agent to be delivered and the required flow rate regime, several microporous membranes can be employed, including asymmetric substrate based films such as cellulose acetate, cellulose acetate buterate, and ethyl cellulose. These membrane films may vary from 20 microns to 100 microns thick and can be made of a porous substrate with a controlled skin where the active porosity can vary from angstroms to 50 microns in diameter. Additionally, other acrylic resins can also be used for thin film, delivery membranes such as poly-methyl-methacrylate (PMM) and polysulfone on PVC also with approximately 2 microns thickness of skin of active membrane surface on up to 100 microns of substrate backing. Other matrix polymer systems are also candidates for microfilm membranes and include PCCE copolyesters and nylon PEBAX-polyethersteramide (PEEA), as well as PTFE, PVDF, P-P mixed ester cellulose and certain other polycarbonates. Manufacturers of these materials include; Bend Research (Cellulose Acetates, polysulfones), Eastman Chemical (PCCE Copolyester #9966), Atochem (PEBAX Nylon), Dupont (Hytrel), Rohm Pharmaceuticals (Acrylic Resins) and Millipore (PTFE), PVDF and mixed ester cellulose).

Considering next the elastic distendable membrane 24, this important component can be manufactured from several alternate materials including rubbers, plastics and other thermoplastic elastomers. These include latex rubber, polyisoprene (natural rubber), butyl rubber, nitrile rubber, other homopolymer, copolymers (random, alternating, block, graft, crosslink and starblock), mechanical poly-blends and interpenetrating polymer networks.

Examples of materials found particularly well suited for this application include; silicone polymers (polysiloxanes) (high performance silicone elastomers made from high molecular weight polymers with appropriate fillers added). These materials are castable into thin film membrances and have high permeability (which allows maximum transport of vapor and gas), high bond and tear strength and excellent low temperature flexibility and radiation resistance. Additionally, silicone elastomers retain their properties over a wide range of temperature ($-80°$ to $200°$ C.) are stable at high temperatures, and exhibit tensile strengths up to 2,000 lb./in$^2$ elongation up to 600%.

Further, silicone (polyorganosiloxanes) are thermally stable, hydrophobic organometallic polymers with the lowest P-P interaction (of all commercially available polymers. This fact coupled with the flexibility of the backbone results in a low Tg ($-80°$ C.) and an amorphous rubbery structure for the high MW (polydimethylsiloxanes). Silicone rubber membranes are considerably more permeable to gases than membranes of any other polymer. Depending on the medicinal fluid used and the filling of the storage mode, which will determine the desired mass transport characteristics of the membrane (permeability and selectivity), other materials of choice include polyurethane-polysiloxane copolymers, blends and IPN's. By example, polydimethylsiloxane (PDMS) and polyurethane (PU) multicomponent IPN containing 10%–20% weight of PU shows enhanced initial modulus relative to that of PDMS itself.

Interpenetrating polymer networks (IPNS) are unique blends of cross-linked polymers containing essentially no covalent bonds, or grafts between them. True IPNS are also homogeneous mixtures of component polymers. Further examples of an additional candidate materials would be a polyurethanepolysiloxane (IPN) bilaminated with a polyparaxylene or alternately bilamination of polydimethylsiloxane (PDMS) and polyparaxylene. Coextruded laminates of this type can be selected according to the desired gas permeability for vapor and $O_2$, $N_2$ and $CO_2$ diffusion and their specific selectivity requirements as well as for direction of gas migration when appropriately layered.

Manufacturers of materials suitable for use in the construction of the distendable membrane, include Dow Chemical, General Electric, B.P. Polymers, Mobay Chemical, Shell Oil Corp., Petrarch Systems, DuPont, Concept Polymers and Union Carbide Corp.

With respect to the structural cover 34, in certain embodiments of the invention, this component can be produced from one of several polymer groups. The plastic structure of this component typically contains an intricate network of open celled omni directional pores. The pores can be made in average sizes for 0.8 micron to 2,000 micron and, gives the porous plastic a unique combination of venting filtering, wicking and diffusing capability and structural strength. Further, the material is strong, lightweight, has a high degree of chemical resistance and depending on the particular configuration of the apparatus, can be flexible. The degree of hardness can range from soft, resilient or rigid, and depending on the specific micro diameter range desired, the following polymers can be employed: Polypropylene(PP), Ultra high molecular weight polyethylene (UHMW PE), High density polyethylene (HDPE), Polyvinylidene Fluoride (PVDF), Ethylene-vinyl acetate (EVA), Styrene Acrylonitrile (SAN), Polytetrafluoroethylene (PTFF). A suitable source of these materials is Porex Technologies of Fairburn, Ga.

An alternate material for use in constructing the covers, as for example, covers 34 and 80, when the cover is to serve as a non-permeable gas barrier, is a material sold by B-P Chemicals International of Cleveland, Ohio, under the name and style "Barex". This material, which can also be used to alternately construct base 14 and element 28, is a clear rubber modified Acrylonitrile Copolymer which has wide application in the packaging industry because of its superior gas barrier, chemical resistance and extrusion (thermoforming) and injection molding capabilities. Structures using this material can be manufactured in either monolayer or coextrusion (with such other materials as polyethylene, polypropylene, polystyrene and other modified styrenes). Combinations of different materials can be used to enhance the desired physical properties of the thermoformed part.

Finally, the foam pad adhesive 38 and peel strip 40 is preferably composed of a thin (1/32") 30 mil closed cell polyethylene (PE) foam double coated with a non-sensitizing acrylic pressure sensitive adhesive (PSA), and 90 lb. white polyethylene coated release liner (peel strip). This foam is also available in 1/16 inch and ⅛ inch thickness. The foam is stretchable, soft, elastic, conformable, cushioning, hypoallergenic, and is desirable for application where sustained use is required. The material is available from the 3M Company of Saint Paul, Minn. and from Betham Corporation of Middlesex, N.J.

Turning now to FIGS. 10 through 17, another embodiment of the invention is thereshown. The apparatus of this form of the invention is similar in many respects to that previously described and like numbers are used to identify like components. Unlike the apparatus illustrated in FIGS. 1 through 9 which has a thermo sealed filling port, the apparatus of this second form of the invention is adapted to be filled using a hypodermic syringe. The device may have a cover made of the same material as cover 34, or may have a different type of impermeable cover, the function of which will presently be described.

Referring to FIG. 10, the apparatus can be seen to comprise a base 14, a distendable member 24 and a flow control member 26 all of which are of the same general character and function in the same manner as in the earlier described embodiment of the invention. The distendable member engaging element 60 is of slightly different construction and includes filling means which enables chamber 25 to be filled using a hypodermic syringe and needle of the character identified in FIG. 17 by the numeral 62. Element 60 is superimposed over flow control member 26 and includes a pair of longitudinally extending, spaced apart upstanding protuberances 64. Each protuberance 64 is provided with fluid passageways 66 which communicate with fluid passageways 16 and 18 provided in base 14. Element 60 also includes an upstanding transversely extending portion 68 having a fluid passageway 70 extending therethrough (FIGS. 10, 11 and 17). In this second embodiment of the invention, the open end 70a of passageway 70 is closed by a septum means for receiving a hypodermic needle. The septum means is here provided as a septum 72 which is adapted to sealably close the open end 70a of passageway 70. Septum 70 is constructed of a self-sealing, puncturable material such as silicone-SEBS (a composite incorporating a silicone interpenetrating network (IPN) into a styrene-ethylene butylene-styrene block copolymer). If desired, the earlier form of the apparatus of the invention as shown in FIGS. 1 through 9 can alternatively have a fill means such as shown in FIG. 17 to permit filling in the field. As best seen by referring to FIG. 12, passageway 70 is in communication with a pair of logitudinally extending passageways 74 formed in element 60. Passageways 74 are, in turn, in communication with chamber 25 via passageways 76.

Cover 80 is formed of a clear plastic material which is impermeable to fluid including gases. This type of cover is used when the medicinal agent within chamber 25 is such that it must be sealed with respect to atmosphere. As best seen in FIG. 18 cover 80 is provided with a pair of longitudinally extending protuberances 82 which are interconnected by a web 84. Web 84 carries on its upper surface an impermeable barrier peel strip 86 that covers vent means provided in web 84 to enable venting of chamber 25 at time of use.

The apparatus of this second form of the invention includes a needle assembly 42 of similar function and construction as that previously described and includes a shielded injection needle 46. The needle assembly is provided with web means and a frangible section 42c to enable portion 42b of the needle assembly to be removed in the manner shown in FIG. 16.

As before, so long as needle assembly 42 remains intact in the manner shown in FIG. 12, the fluid will be retained within chamber 25. However, upon twisting off the frangible section 42c so that portion 42b on the needle assembly can be removed as shown in FIG. 16, distendable membrane 24 will begin to expel fluid through the needle 46. The rate of expulsion of fluid is, of course, controlled by the permeable membrane 26 which is disposed intermediate the fluid flow passageways 66 of member 60 and fluid flow passageways 16 and 18 formed in base 14.

Referring to FIGS. 18 through 21, another embodiment of the invention is thereshown. The apparatus of this form of the invention is similar in many respects to the embodiment shown in FIGS. 1 through 9 and like numbers are used to identify like components. Unlike the apparatus illustrated in FIGS. 1 through 9, the apparatus of this third form of the invention does not embody an injection needle assembly. Rather, the device of this embodiment includes a luer connector assembly 90, the function of which will presently be described.

Turning particularly to FIG. 18, the apparatus can be seen to comprise a base 14, and an operating assembly 92 associated therewith comprising a distendable member 24, a distendable member engaging element 28, a flow control member 26 and a cover 34, all of which are of the same general character and function in the same manner as the embodiment of the invention shown in FIGS. 1 through 9 The device also includes an adhesive foam pad 38 and a peel strip 40 carried by base 14.

The luer connector assembly 90, which comprises the distinguishing feature of this form of the invention, is integrally formed with base 14 and includes a distal portion 90a and a proximal portion 90b. Distal portion 90a is provided with a longitudinally extending bore 94 which communicates with outlet 22 of base 14. Comprising the proximal portion 90b of assembly 90 is a luer connector of standard construction having a fluid passageway 96 which communicates with bore 94 of distal portion 90a. The outlet of passageway 96 is sealed by a frangible closure which is removable to activate fluid flow. The outboard end of distal portion 90a, designated in the drawings as 90c is of reduced diameter and is readily flexed to permit easy connection of the luer connector "L" with an external system "E" (FIG. 20).

As shown in FIGS. 18 and 21, base 14 includes fluid conduits 16, 18 and 20 which communicate with outlet passageway 22. Distendable membrane 24 functions to expel fluid from chamber 25, through flow rate control member 26 and outwardly through outlet passageway 22 in the manner previously described.

Referring to FIGS. 22 through 29 yet another form of the invention is shown and identified by the numeral 100. For certain medicinal agents, it is desirable to provide an initial high rate delivery followed by a slower rate sustained delivery. This form of the invention permits this to be accomplished. The apparatus of this form of the invention is similar in many respects to the embodiment shown in FIGS. 1 through 9 and like numbers are used to identify like components. Unlike the apparatus illustrated in FIGS. 1 through 9, the apparatus of this fourth form of the invention is not limited to a fixed rate infusion of the medicinal agent. Rather, because of the novel configuration of the distendable membrane engaging element and the dual flow rate control members of this form of the invention, a controlled variable rate of fluid flow is possible.

As best seen in FIGS. 22, 23 and 24, the apparatus of this last form of the invention also comprises a laminate, or layered, structure made up of a plurality of thin plate-like components. The apparatus includes a thin, generally planar plate-like base 102, having a transverse recess 104 in communication with a fluid outlet passageway 106. A thin, generally planar elastic distendable membrane, or member 108 cooperates with base 102 to form a pair of discrete chambers 110 and 111 (FIG. 27). For certain applications, Chambers 110 and 111 may be of different individual size and configuration each having different volumes. As before, member 108 is distendable out of plane in the manner shown in FIG. 25 by the introduction of fluid into the chambers under pressure. The method of introduction of fluids into chambers 110 and 111 will presently be described.

Forming an important aspect of the apparatus of this fourth form of the invention is the provision of flow control means which are disposed internally of chambers 100 and 111 for controlling the rate of fluid flow of fluid from each chamber through outlet 106. In the embodiment of the invention hereshown, the flow control means is provided in the form of a flow rate control assembly 112 which is received within recess 104 formed in base 102 in the manner shown in FIGS. 22 and 24. Flow rate control assembly 112 includes a pair of permeable members 114 and 116 which, as will presently be described, precisely control the rate of fluid flow from chambers 110 and 111 into fluid outlet 106. Passageway 106 is in communication with the fluid passageway of needle assembly 42 which is of the same construction as previously described herein.

As best seen in FIG. 24, assembly 112 comprises a manifold member 118 which is closely receivable within recess 104 formed in base 102. Member 118 is provided with an internal fluid conduit 120 having fluid inlets 122 and 124 at either end and a fluid outlet 126 proximate its center. Outlet 126 is adapted to communicate with outlet passageway 106 provided in base 102 when member 118 is in position within recess 104. Permeable members 114 and 116 overlay inlets 122 and 124 and, in a manner presently described, control the flow of fluid into these outlets from chambers 110 and 111. Fluid inlets 122 and 124, can be constructed in various geometries and, in cooperation with the ullage means, presently to be described, to provide various degrees of active surface area of the rate control membrane.

The distendable member engaging element 130 of this latter form of the invention is of slightly different construction and includes filling means which enable chambers 110 and 111 to be filled separately. As best seen in FIGS. 22 and 25, element 130 is superimposed over base 102 and flow control assembly 112 and includes a pair of longitudinally extending, spaced apart upstanding protuberances 132 and 134. Protuberances 132 and 134 are provided with fluid passageways 136 and 138 respectively. Passageway 136 communicates with fluid inlet 122 and passageway 138 communicates with inlet 124 of assembly 112. By varying the configuration of these passageways and fluid inlets alternate active surface areas of the flow control membrane can be exposed. Element 130 also includes an upstanding transversely extending portion 140 having a pair of fluid passageways 142 and 144 extending from the open ends 142a and 144a thereof. As shown in FIG. 23, passageway 142 is in communication with passageway 136 of element 130 via a passageway 152 and passageway 144 is in communication with passageway 138 of element 130 via a passageway 148. Passageways 146 and 148, in turn, communicate with chambers 110 and 111, respectively, via passageways 150 and 152 respectively (see FIGS. 25 and 26). Open ends 142a and 144a of passageways 142 and 144 are closed by any suitable means such as heat sealing.

The apparatus of this fourth embodiment of the invention is adapted to be filled with the selected medicinal fluid at time of manufacture. This is accomplished by forcing fluid under pressure into passageways 142 and 144, and thence, into chambers 110 and 111 via passageways 150 and 152. As the fluid under pressure flows into the two chambers, it will cause the membrane 108 to distend upwardly into engagement with cover 34 in the manner shown in FIG. 27. After chambers 110 and 111 have been filled with the selected medicinal fluid, passageways 142 and 144 are sealably closed. Cosmetic closure plugs 154 and 156 can be used if desired at the ends of conduits 142 and 144. It is to be observed that membrane 108 is bonded along its margins 108a to member 130 and is in sealable engagement along its longitudinal center line with member 130 intermediate protuberances 132 and 134. With this construction, chambers 110 and 111 are maintained independent from one another.

Upon twisting off the frangible section 42c so that portion 42b on the needle assembly can be removed as shown in FIG. 29, elastic distendable membrane 108 will begin to expel fluid through flow control members 114 and 116. The rate of flow of fluid is, of course, controlled by the degree of permeability of each of the members 114 and 116. If one of these members has a greater permeability than the other, fluid will flow through that member at a greater rate. Accordingly, by varying the permeability of members 114 and 116, and with the output summed via flow channels 120 and 106, a larger initial volume of fluid can be injected into the patient. Continuous injection of fluid at a slower controlled rate will then follow. For example, if member 114 has a high degree of permeability, fluid will be forced out of chamber 110 at a rapid rate. On the other hand, if member 116 has a low permeability, fluid will be forced out of chamber 111 at a slower rate. With this arrangement, fluid can be simultaneously injected initially at a high rate from chambers 110 and 111 then at a much slower rate from chamber 111.

As indicated in FIG. 22, the apparatus is closed by a cover 34 having a medicant label 36. If a barrier cover and base configuration is used, cover vent means as previously described, must be provided. Affixed to the bottom of the base is an adhesive foam pad 38 and a peel strip 40 so that the apparatus can be self-attached to the patient.

Figure 30B:
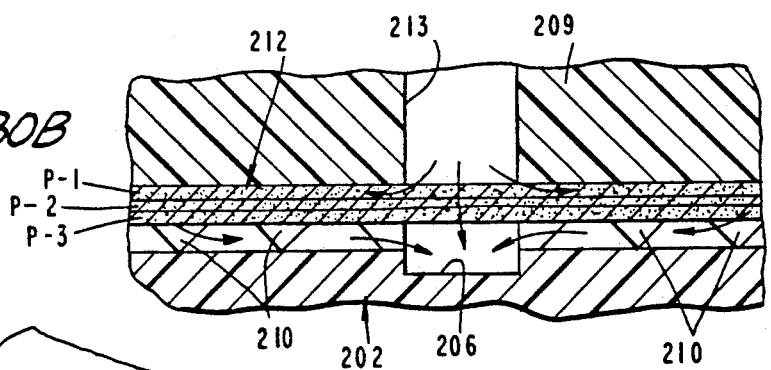
FIG. 30B is an enlarged cross-sectional view of the circled area shown in FIG. 32.

Turning now to FIGS. 30, 31, and 32, another embodiment of the apparatus for use in infusing medicinal fluids into a patient is there illustrated and generally designated by the numeral 200. The device of this form of the invention is similar in many respects to that shown in FIGS. 18 through 21 and like numbers are used to identify like components. As best seen by referring to FIG. 30, the apparatus comprises a thin, generally planar plate-like base 202 having at least one flow rate control channel. In the form of the invention shown in FIGS. 30 and 30A, the base is shown as having a pair of flow rate control channels provided here as longitudinally extending fluid conduits 204 and 206. Conduits 204 and 206 are interconnected by a fluid transfer manifold, or transverse conduit 208, which, in turn, is interconnected with a fluid outlet passageway. Distendable membrane engagement means, shown here as protuberances 209, perform the same function as protuberances 30 previously described. It is to be understood that in some applications only a single protuberance is provided and in other applications no protuberance at all is required.

A thin, initially generally planar distendable elastomeric membrane, or member, 24 (FIG. 32) cooperates with base 202 to form a chamber 25 (FIG. 32). Member 24 is distendable in the manner shown in FIG. 32 by the introduction of fluid into the chamber under pressure. As previously described herein, as the distendable member 24 is distended by the fluid pressure, internal stresses are formed in the member which continuously urge it toward engagement with protuberances 209 as it trys to return to its original configuration. The method of introduction of fluids into chamber 25 is as previously described in connection with the embodiment of FIGS. 12 through 21.

An important feature of this latter embodiment of the invention is the provision of a multiplicity of flow rate control micro-channels 210 in base 202. Micro-channels 210 are disposed on either side of conduits 204 and 206 and communicate therewith via flow control means of a character presently to be described.

In the embodiment of the invention shown in FIGS. 30 through 32, the flow control means is provided in the form of a thin, multilayered or gradiated assembly 212 which is superimposed over channels 210 in the manner shown in FIG. 32. With this construction, when the device is in a fluid discharge mode, fluid within chamber 25 is forced by membrane 24 through channels 213 provided in protuberances 30, through assembly 212, through micro-channels 210, into conduits 204 and 206 and outwardly through outlet passageway 214. Passageway 214 is connected with dispensing means shown here as luer connection assembly 90 which includes a fluid flow conduit and fluid dispensing port or luer connector "L". By controlling the area of the micro-channels, the active surface area of membrane assembly 212 which is exposed to fluid can be varied in a manner to optimize fluid flow through assembly 212. Similarly by controlling the size and shape of the micro-channels, the rate of flow of the fluid through membrane assembly 212 can also be uniformly maintained.

As indicated in FIG. 31, the flow control means of this form of the invention, rather than consisting of a single layer of a permiable material having the desired fluid flow characteristics, here comprises an assemblage of a plurality of layers of permiable materials, P-1, P-2, and P-3, each having selected characteristics. These layers, which may be composites, thin films, or porous substrates, may be constructed of any of the materials previously described herein so that the fluid pressure flow characteristics of the assemblage can be optimized for the particular medicinal or other fluid being dispensed. For example, layer P-1 may comprise an asymmetric membrane, or film, having a first porosity, P-2 may comprise a resin membrane or film having a second porosity and layer P-3 may comprise a carrier substrate of predetermined porosity. In another application P-1 and P-3 may take the form of carrier substrates and P-2 may comprise a very thin, rate control element. In this way a unique composite, sandwich-like assemblage can be constructed. In certain applications assembly 212 can be constructed with gradient layers rather than with discrete elements in a manner to produce comparable results.

The multilayered, or gradient layer construction described in the preceding paragraph permits easier, thin-film manufacture, precise flow control over extended periods and easier handling of the membrane film during system manufacture.

Referring next to FIGS. 33 through 39, still another embodiment of the present invention is there shown. This embodiment of the invention is also similar to that shown in FIGS. 18 through 21 and like numerals are used to identify like components. As best seen in FIG. 33, the device comprises a base 300 having a pair of flow rate control channels 302 and 304 and a transversely extending fluid transfer manifold conduit 306. Conduit 306 is connected with an outlet 300 (FIG. 34) which, in turn, is in communication with a fluid dispensing means, shown here as a fluid dispensing port 312.

Unlike the embodiments of the invention previously described, the device of this form of the invention does not include a flow rate control membrane of the character previously described. Rather, the rate of fluid flowing from the dispensing means of the device is controlled by flow control means disposed intermediate outlet 310 and fluid dispensing port 312. The flow rate control means is here provided as a fluid flow micro-conduit 314 and a porous member 316 (FIG. 36) which functions to restrict the flow of fluid between outlet 310 and dispensing port 312.

Figure 39:
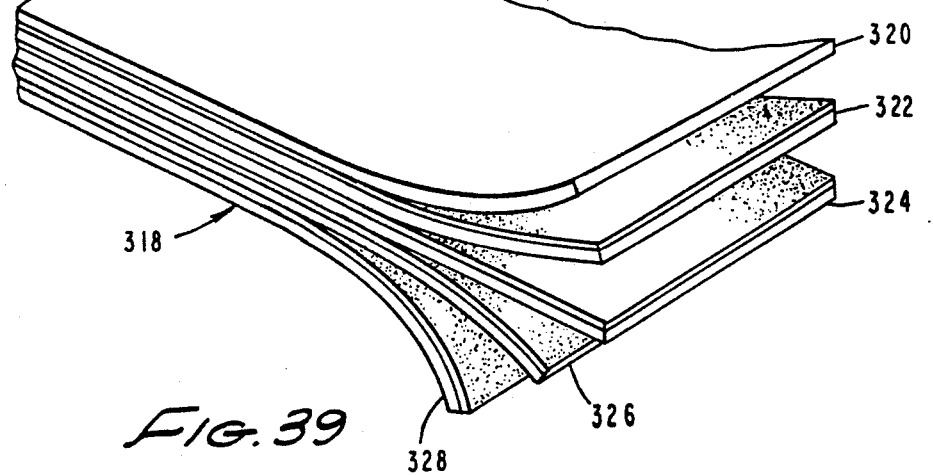
FIG. 39 is a fragmentary, generally perspective view of the distendable membrane of the latest form of the invention illustrating the laminate construction thereof.

Another critical difference between the embodiment of the invention now being considered and the previously described embodiments resides in the unique character of the stored energy means used for discharging fluid from the device. Here the stored energy means, rather than being a single isotropic, elastomeric distendable membrane, comprises a laminate assemblage made up of a plurality of initially generally planar distendable elements or films. Referring particularly to FIG. 39, the stored energy means is there shown as a laminate assemblage 318 made up of individual elements or membranes 320, 322, 324, 326 and 328. Assemblage 318 functions in much the same way as the earlier described distendable membranes, and uniformly cooperates with base 300 to define fluid chambers or reservoirs 25. However, by constructing the stored energy means from a composite of several distinct elements or layers, the elastic characteristics of the stored energy means can be precisely tailored and the stored energy means can be uniquely constructed to function also as a gas permeability valve as well as the means for expelling fluids from the fluid reservoir. This unique, multilayered or gradient construction permits venting to atmosphere through the membrane surface certain selected, entrained gases or vapors in the reservoir while simultaneously precluding any negative migration of selected atmospheric gases or vapors into the reservoir. Where the composite is made up of two or more layers of alternating thickness and premeability, and the permeability constants of the individual film layers are pressure dependent, the permeability of the stored energy means is effected and the direction of flow of the permiant through the membrane wall is controlled by the order in which the individual layers or gradiations of the composite are assembled.

For example, referring to FIG. 39, layer 320 which may be distal to the reservoir comprises a thin film elastomer of a first thickness and a first permeability. On the other hand, layer 328, which may be proximal to the reservoir, comprises a thin elastomer film of a second thickness and a second permeability. Layers 322, 324 and 326 may be of further alternating thickness and permeability and, if desired, may also have different perm-select characteristics. The selective arrangement of the different films each with its own individual permeability constants in ascending order, will dictate the direction of flow of selected gases and vapors through the stored energy means.

Turning now to FIGS. 40 through 45, another embodiment of the apparatus for use in infusing beneficial agents into a patient is there illustrated. The device of this form of the invention is unique in that it provides the opportunity to add to the diluent or other parenteral fluid being introduced into the device selected elements, chemical compounds and biologically active materials such as drugs, medicaments, biological agents, or other therapeutic agents (additives). This addition is accomplished by removably affixing the selected additives to various forms of support structures which can be placed within the path of the fluid flowing through the device so that upon contact with the fluid, the additives are released at a controlled rate to the fluid. In this way, the delivery system of the invention can be safely rendered therapeutically active upon hydration of the additive with a selected parenteral fluid such as a sterile diluent or other acquous solvent.

The basic structure of the device of this new form of the invention is similar in many respects to that shown in FIGS. 18 through 21 and in FIGS. 33 through 39 and like numbers are used to identify like components.

As best seen by referring to FIG. 41, the apparatus comprises a base made up of a first, generally planar member 400 and a second companion member 401 which includes a pair of longitudinally extending flow rate control conduits or channels 402 and 404 which communicate with a transversely extending fluid transfer manifold conduit 406 (FIG. 40). Conduit 406 is, in turn, connected with a fluid outlet 408 which is in communication with a fluid dispensing means shown here as including a fluid dispensing port 410.

First base member 400 is also provided with a pair of longidutinally extending manifolds 411 which communicate with micro-channels 412 (FIG. 44). As best seen in FIG. 42, manifolds 411 and micro-channels 412 communicate with conduits 402 and 404 via flow control means of the general character described in connection with the embodiment of the invention shown in FIGS. 30 through 32. More particularly, the flow control means is here provided as a thin, multilayered or gradiated assembly 212 (see FIG. 31) which is superimposed over manifolds 411 and micro-channels 412 in the manner shown in FIG. 41. Assembly 212 comprises an upper microporous layer, an intermediate rate control membrane and a lower support layer. With this construction, when the device is in a fluid discharge mode, fluid which is contained within chamber 25 (FIG. 44), such as a diluent containing the additive (the beneficial agent) is initially forced by the stored energy means through channels 414 provided in a pair of upstanding protuberances 416 formed on base member 401. As the liquid passes through channels 414, it enters a pair of longitudinally extending manifolds 417 which are formed in base member 401 and which align with manifolds 411 formed in base member 400. Manifolds 417 function to uniquely distribute the fluid as it flows toward the flow control assembly 212 in a manner to disperse the fluid throughout a wide area of the flow control assembly. The uppermost layer of the assembly is designed to permit multi-axial flow distribution thereby effectively utilizing an extensive surface area of the rate control membrane. The beneficial agent flows through the rate control membrane layer, through the support layer, through micro-channels 412, and thence outwardly through outlet passageway 408. Passageway 408 in turn communicates with dispensing means, shown here as including a connector assembly 90.

As previously discussed, by controlling the area of the manifolds, the character of the uppermost layer of the flow control means, and the area of the micro-channels, the active surface area of the rate control membrane which is exposed to fluid can be precisely varied in a manner to predictably achieve the desired fluid flow control. Certain regimes of the various layers of assembly 212 can be rendered hydrophillic or hydrophobic by the appropriate use of materials and coatings in a manner and in amounts well known in the art. In this way, the wettability of the assembly can be precisely tailored as well as the initial gas venting capability of the system.

The distendable membrane engagement means, shown here as protuberances 416 (FIG. 41) perform the same function as previously described. It is to be understood that in some applications only a single protuberance is provided and in other applications no protuberance at all is required.

The stored energy means of this embodiment is of the same character as shown in FIG. 39 and comprises a laminate assemblage 318 made up of individual elements or membranes 320, 322, 324, 326 and 328. Assemblage 318 functions in much the same way as the earlier described, single layer distendable membranes, and uniformly cooperates with base member 401 to define fluid chambers or reservoirs 25 (FIG. 44). However, as previously mentioned, by constructing the stored energy means from a composite of several distinct members or layers, the elastic characteristics and the resultant energy flux of the stored energy means can be precisely tailored. In this way, the stored energy means can also be uniquely constructed to function as a gas permeability valve (for example to prevent external negative migration of fluids into the reservoir) as well as the means for expelling fluids from the fluid reservoir.

As indicated in FIG. 41, superimposed over the base and the stored energy source is a structural cover 34 of the character previously described having appropriate medicant and use labels 36. Affixed to the bottom of base member 400 is a cushioning means or pad 38 having adhesive on both sides. A peel strip 40 is connected to the lower surface of pad 38. For certain applications, a thin protective film may be affixed over cover 34 to prevent ingress of liquids or other contaminants into the device.

Like the apparatus shown in FIG. 10, the present embodiment includes filling means which enables chambers 25 to be filled with a selected parenteral liquid using a hypodermic syringe and needle of the character identified in FIG. 17 by the numeral 62 (see also FIG. 43). To accomplish filling of the chambers, base member 401 includes an upstanding transversely extending portion 418 having a fluid passageway 420 extending therethrough. In this embodiment of the invention, the open end 420a of passageway 420 is closed by a septum means for sealably receiving a piercing element such as a hypodermic needle. The septum means is here provided as a needle septum 422 which is adapted to sealably close the open end 420a of passageway 420. Septum 422 is preferably constructed of a self-sealing, non-coring, puncturable material such as silicone-SEBS. It should also be understood that the septum means can also take the form of a split septum for use with a state-of-the-art blunt cannula injector system. As best seen by referring to FIG. 40, passageway 420 is in communication with longitudinally extending channels 402 and 404. As before, channels 402 and 404 are, in turn, in communication with chambers 25. With this construction, an appropriate injectable such as a diluent or parenteral fluid contained within syringe 62 can be introduced into chambers 25 via passageway 420.

Before considering the highly important adding means of this latest embodiment of the invention a brief introductory background is perhaps helpful.

In the past it has been common practice to mix various types of separately packaged drugs with a suitable diluent immediately before they are delivered intravenously to a patent. Typically the drugs are packaged separately from the diluent for various reasons. For example, many drugs do not retain their chemical and physical stability when mixed with a diluent and thus cannot be stored for any substantial period of time. Also, drugs are often packaged separately from the diluent because many firms which manufacture drugs are not engaged in the business of providing medical solutions in containers for intravenous delivery and vice versa.

Traditionally, the mixing of the drug and the diluent was accomplished by a doctor, nurse or medical professional injecting the injectable fluid into a glass vial containing the drug. After mixing of the drug and the diluent, the solution thus formed is withdrawn into a syringe barrel and in some instances injected immediately into the intravenous system of a patient. More typically however, the reconstituted drug is injected from the syringe into a larger container of solution for connection to an intravenous administration set. This prior art procedure is time consuming, imprecise and generally undesirable.

The device of this latest form of the invention elegantly overcomes the drawbacks of the prior art reconstituting and delivery techniques by providing in conjunction with the basic fluid delivery device of the invention a simple and precise means for automatically mixing the desired drug with the appropriate diluent at the time the device is charged.

In the paragraphs which follow, wherein the details of this unique reconstitution process will be discussed, the following terms will have the following meanings:

Element—any of the fundamental substances that consist of atoms of only one kind and that singly or in combination constitute all matter.

Additive—the element, compound, substance, agent, biologically active material, or other material which is to be added, all or in part, to the fluid introduced into the device of the invention.

Polymer—a chemical compound or mixture of compounds formed by polymerization and consisting essentially of repeating structural units.

Parenteral Fluid—any solution which may be delivered to a patient other than by way of the intestines, including water, saline solutions, alkalizing solutions, dextrose solutions acidifying solutions, electrolyte solutions, reagents, solvents and like acquous solutions.

Beneficial Agents—any drug, medicament, pharmaceutical, medical polymer, enzyme, hormone, antibody, element, chemical compound or other material useful in the diagnosis, cure, mitigation, treatment or prevention of disease and for the maintenance of the good health of the patient.

Biologically Active Material—a substance which is biochemically, Immunochemically, physiologically, or pharmaceutically active or reactive. Biologically active material includes at least one or more of the following: biochemical compounds (such as amino acids, carbohydrates, lipids, nucleic acids, proteins, and other biochemicals and substances which may complex or interact with biochemical compounds), such biochemical compounds biologically functioning as antibodies, antigenic substances, enzymes, cofactors, inhibitors, lectins, hormones, hormone producing cells, receptors, coagulation factors, growth enhancers, histones, peptides, vitamins, drugs, cell surface markers and toxins, among others known to those skilled in the art. Of the group of biologically active materials described, proteins are of utmost current interest because of the large molecule genetically engineered biopharmaceuticals as those species to be immobilized and congregated on the additive carriers hereinafter to be described. A discussion of the use of biomosaic polymers as carriers for biologically active materials is set forth in European Patent Application 0,430,517 A2.

Adding Means—an additive and any means for presenting the additive to the fluid flowing through the fluid passageways of the fluid delivery device of the invention in a manner such that all or any part of the additive will be added to the fluid. The adding means comprises the additive and the additive presentation means which may take the form of a functional support, or carrier, an anchorage, a deposition or reaction site or an element holder with or without some type of intermediate matrix or other release composition.

Additive Presentation Means—Any means such as a functional support or substrate for presenting the additive to the fluid flowing through the device. The functional substrate can comprise a polymer, copolymer, an inter-polymer, a ceramic, a crystal sponge, a carbon based matrix, a celullosic, glass, plastic, biomosaic polymers, azlactone-functional polymer beads, adduct beads, carboxylate-functional polymer beads, gums, gells, filaments and like carriers.

By way of illustration, the adding means of the invention can take several different forms such as those illustrated in FIGS. 43 and 45. However, in its preferred form, the adding means includes a cylindrically shaped, functional support structure which is inserted into passageway 420 and to which various additives, including beneficial agents such as drugs, biologically active materials, and chemical elements and compounds can be releasably connected. These additives are carried by the structure in a manner such that, as the liquid flows through passageway 420 and circulates through the support assembly in the manner shown by the arrows in FIG. 43, the additives will be presented to the liquid flow and efficiently added to the liquid as it flows toward chambers 25.

The additives themselves can also take various physical forms including liquid, solid, granular, powder, particle, gel, wax, hydrocolloid carrier, a gum, film, tablet, crystalline, emulsions, microcrystalline, microspherical, spray dried compounds and lypohilized compounds and saturants. The additives can be removably connected to, immobilized on, impregnated within or supported by the support means in a number of ways. The additives can be chemically or mechanically attached, affixed, or bound directly or indirectly, linked or cross linked, anchored to the surfaces of the support, or surface active agent or they can be absorbed, reaction catalyzed, electrostatically encapsulated, attached by chemical modification or transformation to the carrier surface, polymerized on or through the carrier, with or without the use of an interpolymer, localized, entrapped, suspended, deposited, impregnated, coated, or occluded or otherwise removably affixed within voids, cells, tubules, and intersticies formed in the support. One important method for removably affixing the additive to the functional support means includes treating the functional support means with a compound having selected reactive functional groups such as azlactone functional compounds with their unique ability to react with aqueous media and their high binding capacity. In this way complexing agents, catalysts and biological materials such enzymes or other proteins, as well as biomacromolecules can be attached to the carrier for later removal and recovering. Additionally, the use of one or more monomeric or polymerized surface active agents allows for rapid dissolution and smooth liberation of the additives. A discussion of such surface active agents is contained in U.S. Pat. No. 4,963,367 issued to Ecanow.

Similarly, the additives can be added to or intermixed with the liquid flowing through the device by one or more of various mechanisms, including mechanical release, chemical reaction, dissolution, disorbsion, debinding, delinking, bioseparation, diffusion, washing, disintegration, errosion, dissassociation, solubilization, leeching, enzymatic cleavage, biological reaction, osmosis, separation from ring opening materials by a ring opening reaction, and other separation means.

Additionally, a polymer can be used as the carrier or support for some component of a reaction system. Three classes of polymeric supports can be used, namely polymeric reagents, polymeric catalysts and polymeric substrates. A discussion of polymers as carriers or supports is contained in *Principles of Polymerization,* Second Edition by George Odian. Microporous polymers usable as carriers are also fully described in U.S. Pat. No. 4,519,909 issued to Castro.

Turning now to FIGS. 41 and 43, one form of adding means, or combination additive carrier and additive is there illustrated and generally designated by the numeral 423. This form of the adding means comprises a generally cylindrically shaped assembly including a substantially cylindrical, porous substrate 423a into which an injector inlet tube 423b is closely received. Surrounding porous substrate 423a is a sleeve 423c having a multiplicity of flow channels 423d. As shown in FIG. 43, the assembly thus formed is inserted into fluid passageway 420 formed in transversely extending portion 418. Receivable within the inlet opening of tube 423b is the previously identified needle septum injection site 422. Connected to portion 418, as by bonding is an insert 424 (FIG. 41) which functions to contain the septum within the device.

In using the apparatus of the embodiment of the invention shown in FIGS. 40-44, septum injection site 422 is penetrated by needle 62 and the sterile diluent is introduced into inlet passageway 420 using the needle syringe. As indicated by the arrows in FIG. 43, as the diluent flows longitudinally of inlet passageway 420 it will pass through porous member 423a, into flow channels 423d and then into chambers 25 urging the distendable membrane 318 outwardly into the position shown in FIGS. 42 and 44. As the liquid flows through porous member 423a, the additives presented to the liquid will be added to the flow, or solubilized by the diluent, thereby activating the diluent to form the therapeutic solution to be dispensed to the patient.

The liquid, such as a parenteral fluid, which is introduced into passageway 418 can include, by way of example, a reagent, a sterile diluent, various electrolytes, aqueous solutions such as aqueous solutions of dextrose, saline solutions, alkalinizing solutions, acidifying solutions, polyonic solutions and any other liquids that can serve as a vehicle for the administration of therapeutic or beneficial agents which are desirable to administer to the patient by infusion.

Turning now to FIG. 45, various other forms of adding means are there illustrated. For example, numeral 425 identifies an assembly comprising a porous substrate with interconnecting voids, such as a crystal sponge 425a, over which various outer coatings 425b exhibiting one or more additives are laminated. The selected additives such as elements, chemical compounds, drugs and functional intermediates are provided on or within the coating layers by techniques well known to those skilled in the art. The additives exhibited by the layers are, of course, introduced into the sterile diluent as the diluent flows along of the inlet passageway 420. In this instance, since the substrate will not be damaged by the needle 62, as might a polymer or celullosic carrier, use of the injector inlet tube 423b is not required.

Another form of additive assembly designated in FIG. 45 by the numeral 427, comprises a solid tubular member having an internal, axially extending fluid passageway 427a, the inner wall of which is lined with a separation coating affixing the additives such as chemical compounds and beneficial agents, or medicaments.

Still another form of additive assembly is identified in FIG. 45 by the numeral 429. This assembly comprises a cylindrical, porous plug like member made up of a multiplicity of fused together microspheres or beads 429a, each of which is coated with a separation or reactive coating upon which is deposited an additive such as a biologically active material or other beneficial agent. The microspheres can be formed of glass, plastic or other suitable materials.

The numeral 431 of FIG. 45 identifies yet another form of the adding means of the invention. In this form of the invention a generally cylindrically shaped functional support means for affinity attachment, and subsequent release of the additive, is formed from a multiplicity of microporous polymers 431a presenting a multiplicity of reactive sites over a wide area for species immobilization. In this form of the invention, in order to avoid needle damage to the polymers, it is necessary to use an injector inlet tube of the character shown in FIG. 41 and identified by the numeral 423b.

The additive assembly designated in FIG. 45 by the numeral 433 may also require the use of an injector tube. This assembly is made up of high porosity, semi-sythetic celullosics 433a formed into a generally cylindrical shape and having interconnecting, interstial surfaces or functional support means and is similar in size and configuration to activating assembly 423.

Another slightly more complex additive assembly is identified by the numeral 435. This assembly is made up of a plurality of spaced apart, porous disk shaped wafers 435a, 435b, 435c, and 435d each wafer being of the same or different construction and porosity and each having reactive sites presenting to the liquid flow specially selected additives such as beneficial agents, elements or compounds so that multiple reactivities and selectivities can be achieved. With this construction, a wide variety of liquid flow rates, and complex sequential separations and priority staged substance introduction into the system reservoir can be achieved by specially designing each of the wafers that cooperate to make up the structural support.

Still another form of activating assembly is designated in FIG. 45 by the numeral 437. This assembly comprises a cylindrically shaped porous structure 437a which is provided with pores of varing sizes only some of which are coated, pluged or impregnated with selected additives 437b and, as necessary, functional intermediate materials.

Finally, the functional support member identified by the numeral 439 exemplifies yet another form of adding means of the invention. This member, which is also of a generally cylindrically shaped configuration, is constructed from a porous ceramic material into which selected additives and intermediate compounds have been removably affixed. Member 439, being made of a hard ceramic, would not be easily damaged by the needle 62 and therefore the injector inlet tube is generally not needed. Member 439 can also be constructed from fuzed activated carbon particles, coated porous zirconium oxide bonded spherules, or other porous forms of polymer reactive supports including joined azlatonefunctional polymer beads suitable for the attachment of functional materials.

Assemblies 423 through 439 which may be soluble or insoluble are intended to merely exemplify, not to limit, the wide variety of materials and constructions that can be used to introduce the desired additives into the liquid flow introduced into the inlet flow passageway 420 of the device.

Turning now to FIG. 46, another form of the invention is shown. This figure shows in cross-section one set of the manifolds 411 and 417 which are formed in base members 400 and 401 of the device. In certain applications, it is sometimes advantageous to provide liquid distribution means within manifolds 411 and 417 to enhance the uniform flow of liquid through the manifolds. In the embodiment of the invention shown in FIG. 46, the liquid distribution means is provided as generally planar strips of felt-like hydrophillic polymer material 440 which is readily wetted by the solution being expelled from chambers 25 by the stored energy means, or distendable membrane 318. Material 440 can be of any type that will enhance the uniform flow of the solution contained within chambers 25 and can include ceramic, crystalline, polymer, sponge and other similar materials which have hydrophillic characteristics.

Figure 47:
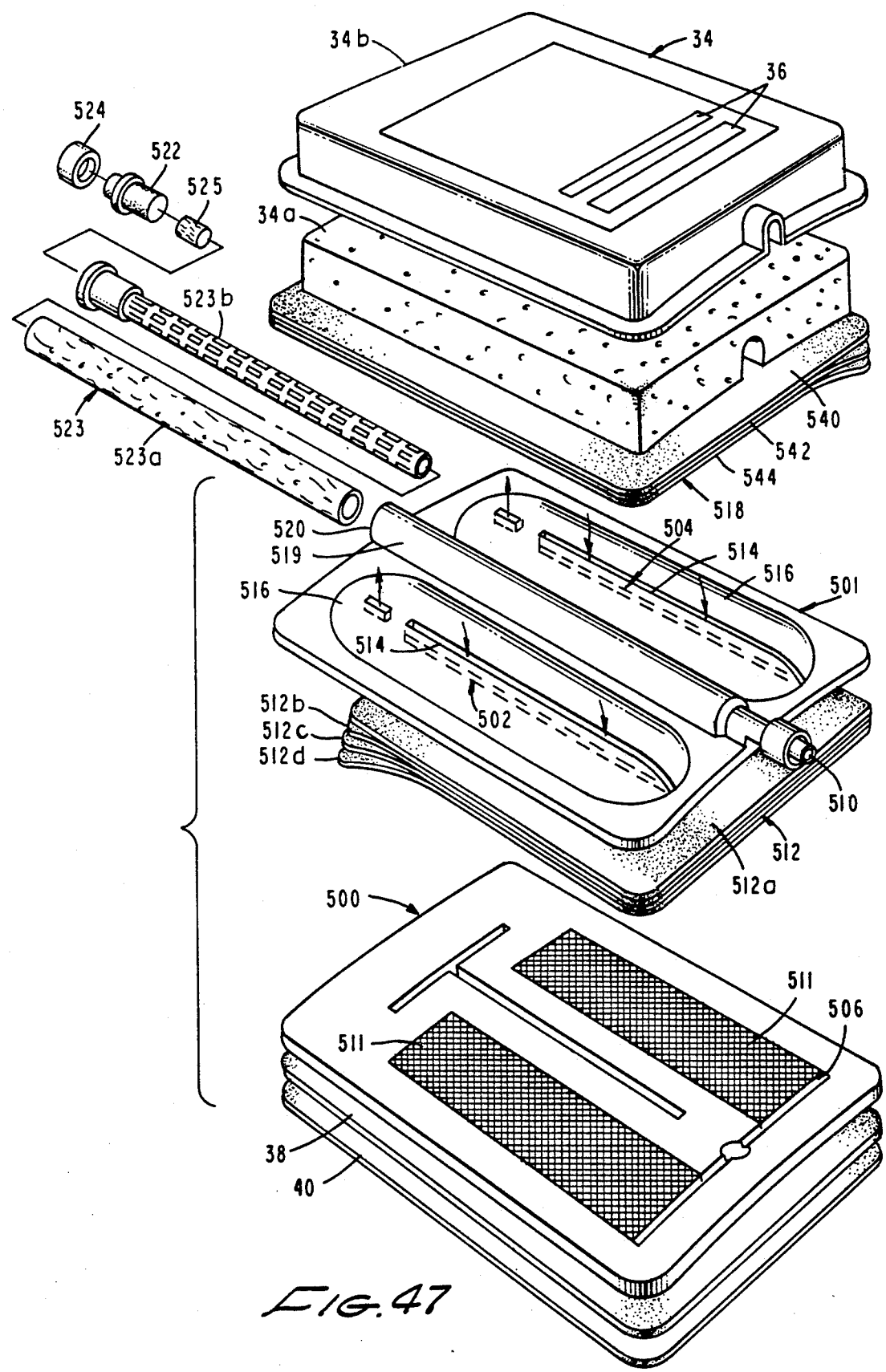
FIG. 47 is an exploded, generally perspective view of yet another embodiment of the invention.

Turning to FIG. 47, another embodiment of the apparatus for use in infusing beneficial agents into a patient is there illustrated. The basic structure of the device of this latest form of the invention is similar in many respects to that shown in FIG. 41 and like numbers are used to identify like components. The major difference between the device shown in FIG. 47 and that shown in FIG. 41 is that the transverse filling portion 418 is replaced by a longitudinally extending filling portion 518. As will be discussed in greater detail hereinafter, the adding means including the additive carriers of this form of the invention are also of a somewhat different configuration.

As in the apparatus of FIG. 41, the apparatus here comprises a base made up of a first, generally planar member 500 and a second companion member 501 which includes a pair of longitudinally extending flow rate control conduits or channels 502 and 504 which communicate with a fluid outlet 508 which is in communication with a fluid dispensing means shown here as including a fluid dispensing port 510.

First base member 500 is also provided with a pair of longidutinally extending manifolds 511 which communicate with micro-channels of the character shown in FIG. 44 and identified by the numeral 412. Manifolds 512 as well as the micro-channels communicate with conduits 502 and 504 via flow control means. The flow control means is here provided as a thin, multilayered or gradiated assembly 512 which is superimposed over manifolds 511 in the manner indicated in FIG. 47. Assembly 512 comprises an upper microporous substrate 512a, an intermediate rate control membrane 512c and a lower support substrate 512d. With this construction, when the device is in a fluid discharge mode, fluid which is contained within chamber 25 (FIG. 44), such as a diluent containing the additive (the beneficial agent) is initially forced by the stored energy means through channels 514 provided in a pair of upstanding protuberances 516 formed on base member 501.

As previously discussed, by controlling the area of the manifolds, the character of the uppermost layers of the flow control means, and the area of the micro-channels, the active surface area of the rate control membrane which is exposed to fluid can be precisely varied in a manner to predictably achieve the desired fluid flow rate control. As before, certain regimes of the various layers of assembly 512 can be rendered hydrophillic or hydrophobic by the appropriate use of materials and coatings in a manner, amount, area and location well known in the art. In this way, the wettability of the assembly can be precisely tailored as well as the initial gas venting capability of the system.

The distendable membrane engagement means, shown here as protuberances 516 perform the same function as previously described. It is to be understood that in some applications only a single protuberance is provided and in other applications no protuberance at all is required.

The stored energy means of this embodiment is also of the same general character as previously described and comprises a laminate assemblage 518 made up of individual elements or membranes 540, 542, and 544. Assemblage 518 functions in much the same way as the earlier described, single layer distendable membranes, and uniformly cooperates with base member 501 to define fluid chambers or reservoirs 25 (FIG. 44). However, as previously mentioned, by constructing the stored energy means from a composite of several distinct members or layers, the elastic characteristics and the resultant energy flux of the stored energy means can be precisely tailored. As before, the stored energy means can also be uniquely constructed to function as a gas permeability valve to control gas flow in one direction as well as the means for expelling fluids from the fluid reservoir.

As indicated in FIG. 47, superimposed over the base and the stored energy source is a cover 34 which includes a porous structural member 34a and a film cover 34b. Appropriate medicant primary labels and instruction for use labels 36 are affixed to cover 34. Affixed to the bottom of base member 500 is a cushioning means or pad 38 having adhesive on both sides. A peel strip 40 is connected to the lower surface of pad 38.

Like the apparatus shown in FIG. 10, the present embodiment includes filling means which enables chambers 25 to be filled with a selected injectable such as a parenteral liquid using a hypodermic syringe and needle of the character identified in FIG. 17 by the numeral 62 (see also FIG. 43). To accomplish filling of the chambers, base member 501 includes the previously mentioned upstanding longitudinally extending portion 519 having a fluid passageway 520 extending therethrough. In this latest embodiment of the invention, the open end of the passageway is closed by a septum means for sealably receiving a piercing element such as a hypodermic needle. The septum means is here provided as a needle septum 522 which is adapted to sealably close the open end of passageway 520. Passageway 520 is in communication with the fluid chambers 25 so that an appropriate parenteral fluid contained within syringe 62 can be introduced into chambers 25 via passageway 520.

One form of adding means and additive carrier of this latest embodiment is generally designated in FIG. 47 by the numeral 523. This form of the adding means comprises an elongated, generally cylindrically shaped assembly including a substantially cylindrical, porous substrate 523a into which an injector inlet tube 523b is closely received. The assembly comprising substrate 523 and injector inlet tube 523b is closely receivable within longtudinally extending fluid passageway 520 formed in longtudinally extending portion 519. Receivable within the inlet opening of tube 523b is the previously identified needle septum 522 which is held in position by insert 524 which is bonded to base member 50.

Disposed intermediate septum 522 and injector inlet tube 523b is a porous flow restrictor 525 which controllably resists the fluid which is flowing into the injector tube. This resistor can be constructed from any suitable porous inert material such as a ceramic or plastic which resists fluid flow in a manner to controllably regulate the residence time of the fluid being introduced into the carrier 523.

As was the case with the embodiment of the invention shown in FIGS. 40 through 45, various additives, including beneficial agents such as drugs, biologically active materials, and chemical elements and compounds can be releasably connected to additive carrier 523. These additives are carried by the structure in a manner such that, as the liquid flows through passageway 520, the additives will be presented to the liquid flow, separated and released and efficiently added to the liquid as it flows toward the reservoir chambers 25.

As before, the additives can take the various physical forms previously described herein and can be removably or releasably connected to the carrier in the many ways previously described. Similarly, the additive can be added to the fluid introduced into the device by the various chemical and mechanical means previously described for easy removal and recovery.

Various other forms of adding means and additive assemblies of the character illustrated in FIG. 45 can also be used with this latest embodiment. For example, a porous substrate with interconnecting voids, such as a crystal sponge 425a over which various outer coatings 425b of one or more additives are laminated can be used. Similarly, a solid tubular member such as member 427 (FIG. 45) having an internal, axially extending fluid passageway 427a, the inner wall of which is lined with a separation coating or surface active agent or intermediate matrix affixing the additives such as medicaments, drugs and other beneficial agents can be used.

Still another form of additive assembly which can be used is of the character identified in FIG. 45 by the numeral 429. This assembly comprises a cylindrical member made up of a multiplicity of fused together microspheres 429a, each of which is coated with a surface active agent separation coating upon which is deposited and chemically anchored a biologically active material or other beneficial agent. Other forms of the additive means which can be used include those shown in FIG. 45 and identified by the numerals 431, 433, 435, 437 and 439.

In certain applications the additive, as defined herein, can be deposited, coated or otherwise removably affixed interstitially of or onto a surface of the membrane 544 of the stored energy means which is exposed to the liquid. With this construction, the fluid entering chambers 25 will be exposed to the additive and the additive will be added to the fluid prior to its infusion into the patient.

Additionally in some applications, the additive can be removably affixed to, impregnated within or otherwise anchored directly or indirectly on or within either or both of the base members 500 and 501. In this way, the additive can be separated from the base members and added to the liquid which contacts the base members at any time prior to its infusion into the patient.

In other applications, the additive can be deposited, coated or otherwise removably affixed interstitially of or onto the rate control assembly 512 so that the additive is exposed to the fluids flowing through the rate control assembly in a direction toward the outlet of the device.

Referring to FIGS. 48 through 60, another embodiment of the apparatus for use in infusing beneficial agents into a patient is there illustrated. The device of this form of the invention is similar in many respects to the embodiment shown in FIGS. 40 through 45 in that it provides the opportunity to add to the diluent or other parenteral fluid being introduced into the device selected elements, chemical compounds and biologically active materials such as drugs, medicaments, biological agents, or other therapeutic agents (additives). However, in this latest form of the invention selected additives are removably affixed to various forms of support structures which are, in turn, contained within a novel additive subassembly that can be inserted into the device in a manner to place the additives within the path of the fluid flowing through the device. In this way the additives, such as drugs, can remain sealed in the prepackaged additive subassembly, which preferably comprises a glass vial, until such time as the subassembly is interconnected with the base of the apparatus and diluent flow through the subassembly is commenced.

Because the basic structure of the device in this latest form of the invention is similar in many respects to that shown in FIGS. 18 through 21, FIGS. 33 through 39 and FIGS. 48 through 54, like numbers are used to identify like components.

Figure 48:
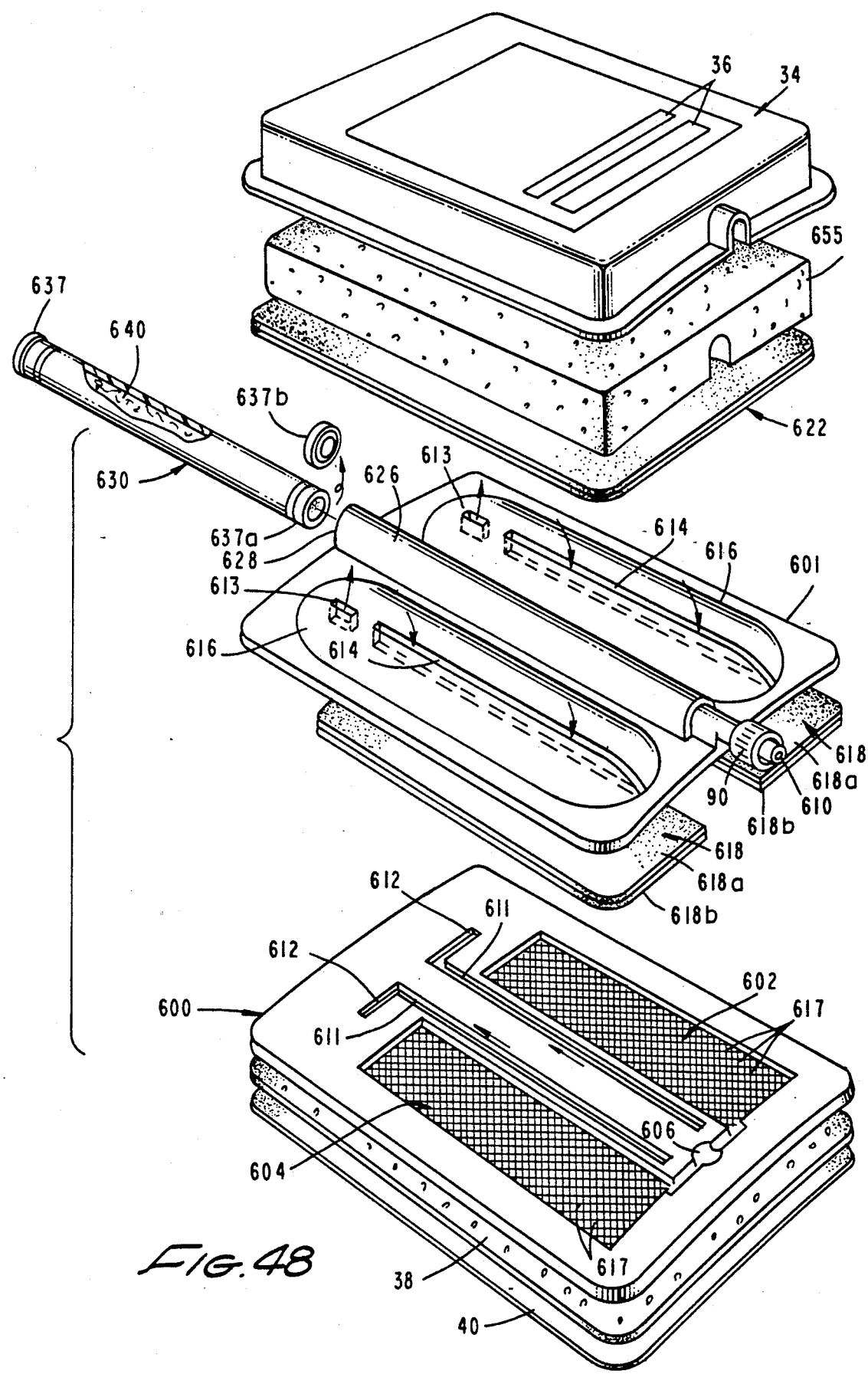
FIG. 48 is an exploded, generally perspective view of still another form of the fluid delivery apparatus of the invention.

As best seen by referring to FIG. 48, the apparatus comprises a base made up of a first, generally planar member 600 and a second companion member 601. Member 600 includes a pair of a longitudinally extending fluid flow manifolds 602 and 604 which communicate with a transversely extending fluid transfer passageway 606 (FIG. 48). Passageway 606 is, in turn, connected with a fluid outlet 608 which is in communication with a fluid dispensing means shown here as including a fluid dispensing port 610 (FIG. 49).

First base member 600 is also provided with a pair of longitudinally extending flow passageways 611 the purpose for which will presently be described. Passageways 611 communicate with a pair of transverse channels 612 (FIG. 48). Channels 612, in turn, communicate with reservoir inlet ports 613 of base member 601 which are of the character best seen in FIG. 48.

Reservoir outlet passageways for fluid flowing outwardly from the reservoir are provided in the form of longitudinally extending flow channels 614 provided in a pair of protuberances 616 which are integrally formed with base member 601. Channels 614, in turn, communicate with microchannels 617 of manifolds 602 and 604 via flow control means, shown here as membrane assemblies 618 (FIG. 48) which are superimposed over manifolds 602 and 604 and micro-channels 617 in the manner shown in FIGS. 48 and 51. Assemblies 618 comprise an upper microporous layer 618a and a lower support layer 618b. With this construction, when the device is in a fluid discharge mode, fluid which is contained within reservoirs or chambers 620 (FIG. 51), such as a diluent containing the additive (the beneficial agent), is initially forced by the stored energy means through channels 614 provided in upstanding protuberances 616 formed on base member 601. As the liquid passes through channels 614, it flows through flow control assemblies 618 and into manifolds 602 and 604. After passing through the flow rate control means, the beneficial agent flows through microchannels 617, and thence outwardly through outlet passageway 606. Passageway 606, in turn, communicates with dispensing means, shown here as including a connector assembly 90.

The distendable membrane engagement means or protuberances 616 perform the sam function as previously described as does the unique stored energy means. The stored energy means of this embodiment is of the general character previously described and comprises a laminate assemblage 622 made up of at least two individual elements or membranes. As before, assemblage 622 cooperates with base member 601 to define the fluid chambers or reservoirs 620 (FIG. 51).

As indicated in FIG. 48, superimposed over the base and the stored energy source is a structural cover 34 of the character previously described having appropriate medicant and medicant use instruction labels 36. Affixed to the bottom of base member 600 is a cushioning means or pad 38 having adhesive on both sides. A peel strip 40 is connected to the lower surface of pad 38. For certain applications, a thin protective film may be affixed over cover 34 to prevent ingress of liquids or other contaminants into the device.

Like the previously described embodiments, the present embodiment includes filling means which enables chambers 620 to be filled with a selected parenteral liquid. Here the filling means includes a hypodermic syringe and needle of the character identified in FIG. 58 by the numeral 62 (see also FIG. 43).

As best seen in FIGS. 48, 53 and 57, base member 601 includes an upstanding, longitudinally extending portion 626 having a generally cylindrical chamber 628 extending therethrough (FIG. 57). In this embodiment of the invention, chamber 628 is uniquely designed to closely receive the additive subassembly that sealably contains the additive to be added to the parenteral fluid.

Referring to FIG. 52, this unique immobilized adding means or additive subassembly comprises a glass tube or vial 630 which is sealed at either end by sealing means shown here as rubber stoppers 632 and 633. Stopper 632 is adapted to sealably receive a piercing element such as the hypodermic needle 62a of syringe assembly 62. (FIGS. 52 and 53). The rubber stoppers 632 and 633 are preferably constructed of a self-sealing, noncoring, puncturable material such as silicone-SEBS. Tear open type aluminum sealing caps 637 are provided at each end of tube 630 and function to sealably encapsulate rubber stoppers 632 and 633.

Sealing caps 637 comprise an aluminum sleeve portion 637a which is crimped in place within a groove 630a provided at either end of tube or vial 630, and a removable end plate 637b. Disposed interiorly of tube 630 is a substrate 640 which releasably carries the additive such as a beneficial agent of the character earlier defined herein (FIGS. 52, 55 and 56). Substrate 640 which, along with the additive, comprises the adding means of this form of the invention can be of the same character as the additive carriers of the assemblies shown in FIG. 45 and identified by the numerals 425, 427, 429, 430, 433, 437 and 439. As indicated in FIG. 59, vial 630 is provided with circumferentially spaced ribs 630b which maintain the substrate spaced apart from the interior wall of the vial. Such stand-off ribs may not be required when substrates of certain character are used.

Turning particularly to FIG. 60, it can be seen that a uniquely configured needle 642 is integrally molded into base member 601. Needle 642 is provided with first and second fluid passageways 644 and 646 which are separated by a center section 645. Passageway 644 is in communication at one of its ends with passageway 650 of base member 601. At its opposite end, passageway 644 communicates with the interior of tube 630 after the needle point 642a has pierced rubber stopper 633 in a manner shown in FIG. 59. Passageway 646 is in communication at one of its ends with passageway 648 of base member 601 and at its opposite end communicates with outlet passageway 608 of base member 601 (FIG. 60).

In using the apparatus of the embodiment of the invention shown in FIGS. 48 through 60, sealing caps 637 are opened in the manner shown in FIGS. 52 and 56 to expose the site injection portion of the rubber stoppers. The adding means, or glass vial 630 is then inserted into chamber 628 and urged forwardly with sufficient force to cause needle 642a to penetrate rubber stopper 633 in the manner shown in FIGS. 57 and 60. As best seen in FIG. 57, vial locking means, here shown as detents 651, are provided at either end of chamber 628. These detents permit passage of vial 630 in an inward direction but function to lock the vial in place to prevent its withdrawal from the chamber.

With the vial locked in place within chamber 628, rubber stopper 632 is pierced by needle 62a of the needle syringe (FIG. 58) and the sterile diluent is introduced into the interior passageway 640a of substrate 640. As indicated by the arrows in FIGS. 49 and 60, as the diluent flows longitudinally of the additive presentation means, or substrate 640, it efficiently intermixes with the additive carried by the substrate. The mixture thus formed flows through passageway 644 of needle 642, into passageway 650 (FIG. 60), through passageways 611 and 612 (FIG. 49) and then into chambers 620 via ports 613. This fluid flow urges membranes 622 outwardly into the position shown in FIG. 51 in close proximity with interior walls 653 of porous body 655.

As before, the liquid, such as a parenteral fluid, which is introduced into passageway 640a can include, by way of example, a reagent, a sterile diluent, various electrolytes and various other aqueous solutions.

After the additive carried by substrate 640 has been separate and released by the parenteral fluid and has been efficiently intermixed therewith, the solution or beneficial agent thus formed will remain within reservoirs 620 until the time it is to be infused into the patient. When the outlet port 610 is opened for fluid flow to the patient, the fluid contained within chambers 620 will flow downwardly through channels 614 in protuberances 616, (FIG. 50), through the flow rate control membranes 618 and into crossing microchannels 617. As best seen in FIG. 48 manifolds 602 and 604 communicate with transverse manifold passageways 606 which, in turn, are in communication with the fluid outlet port 610 of the device. A hydrophilic porous flow filter 659 is disposed proximate the outlet end of substrate 640 (FIG. 55) for filtering and controlling the residence time of the fluid within the substrate 640.

It is to be appreciated that a wide variety of additives, such as drugs and the like, can be removably affixed to substrates of widely varying material composition and design. The substrates can then be safely sealably contained within the sealed glass vial of the additive subassembly for use at any later time with stored energy infusion devices of the character shown in FIG. 48. This unique approach provides a completely new dimension to the preparation, packaging and controlled administration of virtually any kind of beneficial agent to an ambulatory patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A device for use in infusing fluids into an ambulatory patient at a controlled rate comprising:
   (a) a base having a fluid inlet and fluid outlet interconnected by a fluid flow path;
   (b) filling means for introducing fluid into said fluid inlet;
   (c) a distendable membrane constructed of an elastic material which is fitted over said base to define a chamber in communication with said fluid inlet and said fluid outlet, said membrane being distendable by fluid introduced into said chamber under pressure through said fluid inlet, said membrane having a tendency to return to a substantially nondistended configuration whereby fluid within said chamber will be expelled through said fluid outlet; and
   (d) adding means disposed within said fluid flow path for adding an additive to fluid flowing therethrough.

2. A device as defined in claim 1 in which said adding means comprises an additive and an additive presentation means for presenting said additive to the fluid, said additive presentation means being disposed within said fluid flow path so that at least a part of said additive will be added to said fluid introduced into said fluid inlet.

3. A device as defined in claim 1 in which said adding means comprises an additive and an additive presentation means for presenting said additive to the fluid, said additive presentation means having exposed surfaces, said additive being removably connected to said exposed surfaces.

4. A device as defined in claim 1 in which said adding means comprises a structural support having exposed surfaces and a beneficial agent present on said exposed surfaces said structural support being disposed within said fluid flow path so that at least a portion of said beneficial agent will be added to said fluid introduced into said fluid inlet.

5. A device as defined in claim 1 in which said adding means comprises a polymer support and an additive carried by said polymer support, said polymer support being disposed within said fluid flow path so that at least a portion of said additive will be added to the fluid flowing through said fluid flow path.

6. A device as defined in claim 1 in which said adding means comprises a member having exposed surfaces and a biologically active material present on said exposed surfaces, said member being disposed within said fluid flow path so that said biologically active material will be added to said fluid introduced into said fluid inlet.

7. A device as defined in claim 1 in which said distendable membrane comprises a plurality of layers of an elastic material one said layer being in contact with the fluid introduced by said filling means.

8. A device as defined in claim 1 further including at least one fluid flow control means disposed internally of said chamber for controlling the rate of flow of fluid toward said fluid outlet.

9. A device as defined in claim 8 further including means disposed intermediate said distendable membrane and said fluid flow control means for creating an ullage within said chamber.

10. A device as defined in claim 8 in which said fluid flow control means comprises a thin film, planar shaped permeable membrane.

11. A device as defined in claim 8 in which said fluid flow control means comprises first and second permeable members, each of said permeable members having different permeability, whereby the rate of fluid flow along said fluid flow path is controllably regulated.

12. A device as defined in claim 8 further including infusion means connected to said fluid outlet for infusing fluid into the patient.

13. A device as defined in claim 12 in which said filling means comprises a self-sealing, puncturable septum disposed within said fluid inlet.

14. A device for use in infusing fluids into an ambulatory patient at a controlled rate comprising:
   (a) a base having a fluid inlet, a fluid outlet and a fluid passageway interconnecting said fluid inlet and said fluid outlet;
   (b) filling means for introducing fluid into said fluid inlet;
   (c) a distendable membrane constructed of an elastic material which is fitted over said base to define a chamber in communication with said fluid passageway, and with said membrane being distendable by fluid introduced into said chamber under pressure through said fluid inlet and having a tendency to return to a substantially nondistended configuration whereby fluid within said chamber will be expelled through said fluid outlet;
   (d) adding means disposed within said fluid passageway for adding an additive to fluid flowing therethrough, said adding means comprising a support and an additive removably connected to said support; and
   (e) infusion means communicating with said fluid passageway for infusing fluid into the patient.

15. A device as defined in claim 14 in which said support has an exposed region, said additive being present at said region, said support being disposed within said fluid passageway so that said additive will be added to said fluid flowing therethrough.

16. A device as defined in claim 15 in which said additive includes an active surface agent.

17. A device as defined in claim 15 in which said support extends transversely of said base.

18. A device as defined in claim 15 in which said support extends longitudinally of said base.

19. A device as defined in claim 15 in which said support comprises a body having interstitial voids.

20. A device as defined in claim 15 in which said support comprises a solid member and in which said exposed region comprises an exposed surface on said member, said additive being deposited on said surface.

21. A device as defined in claim 15 in which said support comprises a body comprising a multiplicity of microporous polymers.

22. A device as defined in claim 15 in which said support comprises a body constructed from high porosity, semi-synthetic celullosics.

23. A device as defined in claim 15 in which said support comprises a plurality of spaced apart porous disk shaped wafers each said wafer having a site exhibiting an additive.

24. A device as defined in claim 15 in which said support comprises a body formed of a porous ceramic material.

25. A device as defined in claim 15 in which said support comprises a crystal sponge.

26. A device as defined in claim 15 in which said support comprises a body constructed from a multiplicity of porous glass beads.

27. A device as defined in claim 15 in which said additive comprises a drug.

28. A device as defined in claim 15 in which said additive comprises a biologically active material.

29. A device as defined in claim 15 in which said additive comprises a chemical compound.

30. A device as defined in claim 15 in which said support comprises an azlactone functional polymer.

31. A device for use in infusing beneficial agents into a patient at a controlled rate comprising:
 (a) a base having a fluid inlet, a fluid outlet and a fluid passageway interconnecting said fluid inlet and said fluid outlet;
 (b) filling means for introducing fluid into said fluid inlet;
 (c) a distendable membrane constructed of an elastic material which is fitted over said base to define a chamber in communication with said fluid passageway, said membrane being distendable by fluid introduce into said chamber under pressure through said fluid passageway and having a tendency to return to a substantially nondistended configuration whereby fluid within said chamber will be expelled through said fluid outlet;
 (d) adding means mounted within said base for adding an additive to fluid introduced by said filling means, said adding means comprising:
  (i) additive presentation means disposed within said fluid passageway for presenting an additive to the fluid flowing therethrough; and
  (ii) an additive removably interconnected to said additive presentation means, said additive comprising a beneficial agent.

32. A device as defined in claim 31 in which said adding means comprises a vial assembly having said additive presentation means sealably contained therein.

33. A device as defined in claim 32 in which said additive presentation means comprises a functional substrate and in which said additive comprises a beneficial agent removably affixed to said functional substrate.

34. A device as defined in claim 33 in which said vial assembly comprises a glass vial having first and second ends sealed by first and second sealing members.

35. A device as defined in claim 34 in which said base includes a longitudinally extending chamber for receiving said glass vial.

36. A device as defined in claim 35 in which a hollow needle is mounted within said longitudinally extending chamber for piercing said second sealing member, said hollow needle having a fluid passageway in communication with said fluid passageway of said base.

37. A device as defined in claim 36 further including vial locking means for locking said vial within said longitudinally extending chamber of said base.

38. A device as defined in claim 36, further including end caps sealably receivable over said first and second sealing members.

39. A device as defined in claim 36 in which said filling means comprises a hollow needle interconnected with a source of fluid, said hollow needle being adapted to pierce said first sealing member of said vial assembly.

40. A device for use in infusing fluids into an ambulatory patient at a controlled rate comprising:
 (a) a base having a fluid inlet and fluid outlet interconnected by a fluid flow path;
 (b) filling means for introducing fluid into said fluid inlet;
 (c) a distendable membrane constructed of an elastic material which is fitted over said base to define a chamber in communication with said fluid inlet and said fluid outlet, said membrane being distendable by fluid introduced into said chamber under pressure through said fluid inlet, said membrane having a tendency to return to a substantially nondistended configuration whereby fluid within said chamber will be expelled through said fluid outlet; and
 (d) adding means disposed within said fluid flow path for adding an additive to fluid flowing therethrough, said adding means comprising an additive and an additive presentation means for presenting said additive to the fluid, said additive presentation means being disposed within said fluid flow path so that at least a part of said additive will be added to said fluid introduced into said fluid inlet.

41. A device as defined in claim 40 in which said distendable membrane includes a surface in contact with the fluid introduced by said filling means and in which said additive is removably interconnected with said surface.

42. A device as defined in claim 40 in which said additive presentation means comprises a flow rate control membrane disposed between said fluid outlet of said base and said chamber, said flow rate control membrane having exposed surfaces, said additive being removably connected to said exposed surfaces.

43. A device as defined in claim 40 in which said additive presentation means comprises a surface on said base, said additive being removably connected to said surface.

* * * * *